United States Patent
Hiles et al.

(10) Patent No.: US 10,071,187 B2
(45) Date of Patent: Sep. 11, 2018

(54) METHODS, SUBSTRATES, AND SYSTEMS USEFUL FOR CELL SEEDING OF MEDICAL GRAFTS

(71) Applicants: Muffin Incorporated, West Lafayette, IN (US); Cook Biotech Incorporated, West Lafayette, IN (US)

(72) Inventors: Michael C. Hiles, West Lafayette, IN (US); Chad E. Johnson, West Lafayette, IN (US); Neal E. Fearnot, West Lafayette, IN (US); Thomas Payne, Pittsburgh, PA (US); Ronald Jankowski, Pittsburgh, PA (US)

(73) Assignees: Cook Biotech Incorporated, West Lafayette, IN (US); Muffin Incorporated, West Lafayette, IN (US)

( * ) Notice: Subject to any disclaimer, the term of this patent is extended or adjusted under 35 U.S.C. 154(b) by 210 days.

(21) Appl. No.: 14/835,005

(22) Filed: Aug. 25, 2015

(65) Prior Publication Data
US 2016/0082157 A1 Mar. 24, 2016

Related U.S. Application Data

(62) Division of application No. 13/115,347, filed on May 25, 2011, now Pat. No. 9,115,336.
(Continued)

(51) Int. Cl.
*A61L 27/50* (2006.01)
*C12M 1/00* (2006.01)
(Continued)

(52) U.S. Cl.
CPC ............ *A61L 27/50* (2013.01); *A61L 27/24* (2013.01); *A61L 27/3604* (2013.01);
(Continued)

(58) Field of Classification Search
CPC .. A61L 27/50; A61L 27/3604; A61L 27/3826; A61L 27/24; A61L 27/3633;
(Continued)

(56) References Cited

U.S. PATENT DOCUMENTS

| | | | |
|---|---|---|---|
| 4,458,678 A | 7/1984 | Yannas et al. | |
| 5,153,133 A | 10/1992 | Schwarz et al. | |

(Continued)

FOREIGN PATENT DOCUMENTS

| | | |
|---|---|---|
| CN | 1868424 | 6/2008 |
| CN | 101195044 A | 6/2008 |

(Continued)

OTHER PUBLICATIONS

Ikuo Yamakawa, "Side Product Utilization: usage Examples of Collagen", Hokkaido University Collection of Scholarly and Academic Papers, Mar. 2004, [Searched on Jan. 19, 2017], No. 11, pp. 4-7, Internet <URL: http://hdl.handle.net/2115/35458>.
(Continued)

*Primary Examiner* — Michael L Hobbs
(74) *Attorney, Agent, or Firm* — Woodard, Emhardt, Moriarty, McNett & Henry, LLP

(57) ABSTRACT

Described are methods, cell growth substrates, and devices that are useful in preparing cell-containing graft materials for administration to patients. Tubular passages can be defined in cell growth substrates to promote distribution of cells into the substrates. Also described are methods and devices for preparing cell-seeded graft compositions, methods and devices for preconditioning cell growth substrates prior to application of cells, and cell seeded grafts having novel substrates, and uses thereof.

18 Claims, 14 Drawing Sheets

Related U.S. Application Data

(60) Provisional application No. 61/348,135, filed on May 25, 2010.

(51) Int. Cl.

| | |
|---|---|
| *A61L 27/24* | (2006.01) |
| *A61L 27/36* | (2006.01) |
| *A61L 27/38* | (2006.01) |
| *C12M 3/00* | (2006.01) |
| *C12M 1/12* | (2006.01) |
| *C12N 5/00* | (2006.01) |

(52) U.S. Cl.
CPC ....... *A61L 27/3633* (2013.01); *A61L 27/3808* (2013.01); *A61L 27/3826* (2013.01); *C12M 21/08* (2013.01); *C12M 23/06* (2013.01); *C12M 23/34* (2013.01); *C12M 25/14* (2013.01); *C12N 5/0062* (2013.01); *A61L 2430/02* (2013.01); *A61L 2430/06* (2013.01); *A61L 2430/26* (2013.01); *A61L 2430/28* (2013.01); *A61L 2430/30* (2013.01); *A61L 2430/32* (2013.01); *A61L 2430/34* (2013.01); *C12N 2533/54* (2013.01)

(58) Field of Classification Search
CPC ............. A61L 27/3808; A61L 2430/30; A61L 2430/32; A61L 2430/34; A61L 2430/02; A61L 2430/06; A61L 2430/26; A61L 2430/28; C12M 23/06; C12M 23/34; C12M 25/14; C12M 21/08; C12N 5/0062; C12N 2533/54
See application file for complete search history.

(56) References Cited

U.S. PATENT DOCUMENTS

| | | | |
|---|---|---|---|
| 5,980,888 | A | 11/1999 | Dimoudis et al. |
| 2001/0014475 | A1 | 8/2001 | Frondoza et al. |
| 2002/0038151 | A1 | 3/2002 | Plouhar et al. |
| 2004/0117033 | A1 | 6/2004 | Frondoza et al. |
| 2005/0025755 | A1 | 2/2005 | Hedrick et al. |
| 2005/0202058 | A1 | 9/2005 | Hiles |
| 2006/0141623 | A1 | 6/2006 | Smith et al. |
| 2006/0258004 | A1 | 11/2006 | Kosnik et al. |
| 2007/0042488 | A1 | 2/2007 | Bornemann |
| 2007/0048383 | A1 | 3/2007 | Helmus |
| 2008/0014181 | A1 | 1/2008 | Ariff et al. |
| 2008/0032398 | A1 | 2/2008 | Cannon et al. |
| 2008/0112998 | A1 | 5/2008 | Wang |
| 2008/0261306 | A1* | 10/2008 | Neumann ............ A61L 27/3808 435/395 |
| 2009/0187257 | A1 | 7/2009 | Fearnot et al. |
| 2009/0204228 | A1 | 8/2009 | Hiles |

FOREIGN PATENT DOCUMENTS

| | | |
|---|---|---|
| JP | S62-122586 | 6/1987 |
| JP | S62-257387 | 11/1987 |
| JP | 2005-523770 A | 8/2005 |
| JP | H08-9961 A | 8/2005 |
| JP | 2009-501562 A | 1/2009 |
| JP | 2009-055817 A | 3/2009 |
| WO | WO 2009/073724 | 11/1987 |
| WO | WO 1996/12510 A1 | 5/1996 |
| WO | WO 2002/07646 A2 | 1/2002 |
| WO | WO 2003/095609 A2 | 11/2003 |
| WO | WO 2004/067733 A1 | 8/2004 |
| WO | WO 2005/023321 A1 | 3/2005 |
| WO | WO 2006/028274 A1 | 3/2006 |
| WO | WO 2007/009036 A2 | 1/2007 |
| WO | WO 2008/124229 A2 | 10/2008 |
| WO | WO 2009/101214 A1 | 8/2009 |

OTHER PUBLICATIONS

The Journal of Kansai Medical University (2008), vol. 59, No. 2, 3, 4, pp. 169-179.
"Cell-Seeded Sutures to Repair the Heart," MIT Technology Review, Internet pages, http://www.technologyreview.com/news/422044 printed Nov. 6, 2012.
Brochure, Amersham Biosciences "Cytopore" Microcarriers for Cell Culture Edition AB 2002.
Brochure, Millipore Corporation, "The Scepter Cell Counter Performs with High Precisionand Speed Across Multiple Cell Lines," 2010.
Fakharzadeh, Michael et al, Poster—"Biological Sutures Can Efficiently Deliver Stem Cells to the Beating Heart," SBE's Second International Conference on Stem Cell Engineering, Boston, MA, May 2010.
Griffith L G: Emerging Design Principles in Biomaterials and Scaffolds for Tissue Engineering, Jun. 1, 2002.
Guyette et al., Abstract, "A novel suture-based method for efficient transplantation of stem cells." J. Biomed Mater. Res. A, Sep. 8, 2012, Internet page http://www.ncbi.nlm.nih.gov/pubmed/22961975 printed Nov. 6, 2012.
Internet Page, http://www3.interscience.wiley.com, Chun et al., "Biodegradable PLGA Microcarriers for injectable Delivery of Chondrocytes: Effect of Surface Modification on Cell Attachment and Function," printed Apr. 27, 2010.
Internet Page, http://www3interscience.wiley.com, Ng, et al., "Optimization of physical parameters for cell attachment and growth on macroporous microcarriers," Abstract 1995.
Internet Pages, http://www.spnngerlink, Wisseman and Jaconson, "Pure Gelatin Microcarriers: Synthesis and Use in Cell Attachment and Growth of Fibroblast and Endothelial Cells," Summary 1985
KeraFast Product Information, Fibrin Microthreads for Stem Cell Delivery, Internet pages https://www.kerafast.com printed Nov. 6, 2012.
Lee Wonhye et al: On-demand Three-dimensional freeform fabrication of multi-layered hydrogel scaffold with fluidic channels.
Lohmeyer et al., Abstract, "Bridging extended nerve defects with an artificial nerve grafting containing Schwann cells pre-seeded on polyglactin filaments." Int. J. Artif Organs, Jan. 2007;30(1):64-74, Internet page http://www.ncbi.nlm.nih.gov/pubmed/17295194 printed Nov. 6, 2012.
Van Eijk et al., Abstract, "Tissue engineering of ligaments: a comparision of bone marrow stromal cells, anterior cruciate ligament, and skin fibroblasts as cell source." Tissue Eng. May-Jun. 2004; 10(5-6):893-903, Internet page http://www.ncbi.nlm.nih.gov/pubmed/15265307 printed Nov. 6, 2012.
Yao et al, Abstract, "Viability and proliferation of pluripotential cells delivered to tendon repair sites using bioactive sutures—an in vitro study." J. Hand Surg Am., Feb. 2011;36(2):252-8, http://www.ncibi.nlm.nih.gov/pubmed/21186083 printed Nov. 6, 2012.
Yao et al., Abstract, "Bioactive sutures for tendon repair: assessment of a method of delivering pluripotential embryonic cells." J. Hand Surg. 2008, 33(9):1558-1564, Internet page http://europepmc.org/abstract/MED/18984338/reload=0;jessionid=zUOyo4NyHqRmbaoS . . . printed Nov. 6, 2012.
English Abstract of CN 101195044.
English Abstract of CN 1868424.
English Abstract of JP2009055817A, dated Mar. 19, 2009, retrieved from Espacenet on Sep. 8, 2017, 1 p.

\* cited by examiner

METHODS, SUBSTRATES, AND SYSTEMS USEFUL FOR CELL SEEDING OF MEDICAL GRAFTS

REFERENCE TO RELATED APPLICATION

This application is a divisional of U.S. patent application Ser. No. 13/115,347, filed May 25, 2011, now issued as U.S. Pat. No. 9,115,336, which claims the benefit of U.S. Provisional Patent Application Ser. No. 61/348,135 filed May 25, 2010 entitled METHODS, SUBSTRATES, AND SYSTEMS USEFUL FOR CELL SEEDING OF MEDICAL GRAFTS, each of which is hereby incorporated by reference in its entirety.

BACKGROUND

The present invention relates generally to medical materials and procedures, and in specific aspects relates to cell-containing medical grafts and methods, substrates and devices useful for preparing them.

The field of tissue engineering has demonstrated significant promise to improve medical treatments for patients across a broad variety of conditions or injuries. One area of study has been that of implantable graft materials that contain viable cells from the patient or from other sources. With regard to the harvest and re-introduction of cells from the patient, termed autologous cellular treatment, methods and systems are known for treating a tissue sample from the patient to result in a cellular preparation that can be re-introduced to the patient. It has been proposed that such methods and systems can be used "bedside" in a hospital setting, e.g. in a single hospital procedure or visit in which the biological tissue sample is obtained from the patient, processed to a cellular composition, and re-introduced into the patient.

In certain modes of use, cells to be introduced into the patient can be combined with a cell growth substrate to form a cell-containing implantable graft. Sometimes, these uses involve a culture period in which the number of cells is expanded after application to the cell growth substrate. Other modes of use do not involve such expansion. Rather, the cells are applied to the cell growth substrate and implanted without a culture period.

Despite demonstrated promise, the clinical implementation of cell-containing graft materials has been slow. Needs exists for more convenient and/or effective ways or materials for combining cells with cell growth substrates so that they are situated for survival and often expansion in the patient. In certain of its aspects, the present invention is addressed to these needs.

SUMMARY

In some of its embodiments, the present invention provides methods, cell growth substrates, and devices that are useful in preparing cell-containing graft materials for administration to patients. Cell growth substrates of the invention can include features enabling their enhanced combination with cell suspensions. In certain embodiments, such features include tubular passages defined in the cell growth substrates to promote distribution of cells during application of cell-suspensions to the substrates. Additional embodiments herein disclosed relate to methods and devices for preparing cell-seeded, flowable matrix graft compositions; to methods and devices for pre-conditioning cell growth substrates prior to application of cell compositions to them; to automated methods and devices for preparing cell-seeded implantable grafts by combining cellular compositions and substrate materials, for example including features for distributing the cells throughout a volume of the substrate materials; and to particulate forms of cell growth substrates and their use to prepare flowable cellular graft materials.

In one particular embodiment, provided is a cell growth substrate for supporting the growth of cells. The substrate includes at least one elongate tubular passage having passage walls defining a lumen extending from a first lumen opening at a surface of the cell growth substrate body into an interior region of the cell growth substrate. The lumen can be configured to receive flow of a cell-containing liquid medium to distribute cells into the interior region of the cell growth substrate. The cell growth substrate can be a cell growth matrix. The substrate can comprise collagen and/or can also comprise a synthetic polymeric tubular element exterior of the substrate and fluidly coupled to the lumen opening. The substrate can include a plurality of the tubular passages. The at least one tubular passage can include at least one primary tubular passage and at least one secondary tubular passage branching from the primary tubular passage. The substrate can comprise a remodelable collagenous extracellular matrix sheet material, and the sheet material can retain growth factors, glycosaminoglycans, and/or proteoglycans from an animal source tissue for the sheet material.

In another embodiment, provided is a method for preparing a cell-seeded material that includes connecting a cell growth substrate, such as one described in the paragraph above, to a source of a liquid suspension of cells, wherein the connecting includes fluidly associating the elongate passage with a transport lumen of the source. The method also includes transporting amounts of the liquid suspension of cells through the transport lumen and into the elongate passage so as to deliver cells to the interior region of the substrate. The connecting step can include inserting the substrate into a cell-seeding chamber having an input tube fluidly connected to the source of liquid suspension of cells, and fluidly coupling the input tube to the first lumen opening of the substrate.

In a further embodiment, provided is a method for preparing a cell-seeded composition for delivery to a patient. The method includes combining a fluid extracellular matrix particulate composition, comprising particles of extracellular matrix and a liquid medium, with a liquid cell suspension to form a cellular fluid composition. The method can also include mixing the cellular fluid composition and/or causing the cellular fluid composition to gel. The gel-causation can include a step of altering the pH of the cellular fluid composition and/or altering the temperature of the cellular fluid composition.

A further embodiment provides a method for preparing and administering a cellular graft. The method includes applying a serum protein composition to a biologically compatible substrate suitable for administration to a patient, to prepare a preconditioned substrate including the serum protein composition and the biologically compatible substrate. Cells are added to the preconditioned substrate to prepare a cellular graft, and the cellular graft is administered to a patient. The applying a serum protein composition step can include spray applying the composition. The step of adding cells can include spraying a liquid cell suspension onto the preconditioned substrate and/or passing a liquid cell suspension into a tubular passage of the substrate.

In another embodiment, provided is a device for seeding a matrix with cells. The device includes a first chamber for receiving a liquid suspension of cells, and a second chamber for receiving a cell growth matrix material to be seeded with the cells. The seeding device further includes a passageway for transfer of amounts of the liquid suspension of cells from the first chamber to the second chamber, a device for detecting at least one condition of the liquid suspension of cells, and an application device for applying the amounts of the liquid suspension of cells to a matrix material received in the second chamber. The application device can include at least one spray nozzle or at least one cannula having a lumen. The seeding device can also include a mechanism for moving the spray nozzle or cannula. Where the application device includes a cannula, the moving mechanism can be operable to withdraw the cannula proximally while dispensing a liquid suspension of cells from an opening of the cannula such as a distal-most opening. The seeding device can also include a registration structure for holding the matrix material in a predetermined position relative to the application device. The seeding device can also include a distribution assist device associated with the second chamber and operable to facilitate distribution of cells within the matrix material after application of the cells to the matrix material by the application device. The distribution assist device can be operable to generate a magnetic field across the matrix material; can be a mixer operable to generate flow in a liquid received in the second chamber; can be operable to generate a pressure gradient within the second chamber; can be operable to move a cell growth substrate received in the second chamber; and/or can be operable to rotate the second chamber to distribute cells within the cell growth matrix material at least partially by centrifugal force. When present, the mixer operable to generate flow can be operable to generate pulsatile, bi-directional flow in a liquid received in the second chamber.

A further embodiment provides a device for preparing a flowable, cell-seeded graft. The device includes a first chamber containing a liquid suspension of cells, and a second chamber containing a flowable cell growth substrate material to be seeded with the cells, the second chamber fluidly connected to the first chamber so that the liquid suspension of cells can be combined with the flowable cell growth substrate material to form a flowable, cell-seeded graft material. The device also includes a mixer operable to mix the flowable, cell-seeded graft material. The mixer can be a static mixer positioned within a flow path for the flowable, cell-seeded graft material, or a rotary mixer. The first and/or second chamber can be a passage.

In another embodiment, provided is a method for preparing a cell-seeded substrate for treating a patient, including a human patient, and potentially also for treating the patient. The method includes processing a tissue sample of the patient to obtain a suspension of cells of the patient, and loading a cell growth substrate into an incubation chamber of a cell seeder device. The method also includes initiating operation of the cell seeder device, wherein the operation causes detection of at least one condition of the suspension of cells, and combination of the cells of the suspension with the cell growth substrate to form a cell-seeded substrate. In a method for treating the patient, the method also includes administering the cell-seeded substrate to the patient.

Also provided is a method for preparing a cell seeded matrix that includes admixing cells with a gellable composition having a first viscosity to form a gellable cell mixture, and applying the gellable cell mixture to a cell growth substrate. The method also includes causing the gellable cell mixture to gel to form a cellular gel in contact with said cell growth substrate. The gel can have a second viscosity which is greater than the first viscosity. The gelling of the mixture can be caused by any suitable measure or combination thereof, including for example altering (e.g. raising or lowering) the pH of the mixture and/or altering (e.g. raising or lowering) the temperature of the mixture. The mixture can be contacted with the substrate so as to provide a layer on an outer surface of the substrate, and/or can be distributed substantially homogenously through the substrate (e.g. where the substrate is porous), or at least a portion of the substrate. Subsequent gelling of the mixture can provide an external cellularized gel layer and/or a cellularized gel distributed substantially homogeneously through all or a portion of the substrate.

In a further embodiment, provided is a cell-seeded graft that includes an extracellular matrix substrate material, a collagenous gel applied to the substrate material, and cells adhered to the substrate material, to the gel, or to both. The collagenous gel can be comprised of an extracellular matrix hydrolysate comprising native collagen and at least one additional native bioactive substance from a source tissue for the extracellular matrix hydrolysate. The at least one additional native bioactive substance can include growth factor(s), glycosaminoglycan(s) and/or proteoglycan(s).

A further embodiment provides a method for preparing a cellular graft for treating a patient, including a human patient, and also potentially for treating the patient. The method includes obtaining serum from the patient, and processing a tissue sample of the patient to obtain a population of cells of the patient. The method further includes applying the serum to a matrix substrate to prepare a serum-preconditioned matrix substrate, and applying the population of cells to the preconditioned matrix substrate to form a cellular graft. In a method for treating the patient, the method can also include administering the cellular graft to the patient.

In a still further embodiment, provided is a method for preparing a material for treating a patient, and potentially also for treating the patient. The method includes combining a suspension of cells with a particulate cell growth substrate, and incubating the suspension of cells in contact with the particulate cell growth substrate to form cellularized particulate bodies having cells attached to particles of the particulate cell growth substrate, wherein the incubating is for a duration and under conditions such that significant expansion of the number of cells does not occur. In a method for treating the patient, the method can also include administering the cellularized particulate bodies to the patient. In certain forms, the incubating of the method can be for a duration and under conditions effective to achieve attachment of at least 20% of the cells in the suspension to the particles but without expansion of the number of cells.

Another embodiment provides a cellular graft for treating a patient, and potentially also use of the cellular graft in a method for treating a patient with the cellular graft, and/or in a method for manufacturing a material for the treatment of a patient. The cellular graft includes cellularized particulate bodies comprised of cells attached to extracellular matrix particles. For use in treatment, the cellular graft can be introduced into the patient.

Another embodiment provides a cellular graft material including a particulate cell growth substrate material and cells attached to particles of the cell growth substrate material. The cells comprise endothelial progenitor cells, muscle derived cells, or a combination thereof. The particles can be particles of a naturally-derived extracellular matrix sheet material isolated from an animal source and optionally processed so as to retain endogenous growth factor(s), glycosaminoglycan(s) and/or proteoglycan(s). Such particles of a naturally-derived extracellular matrix sheet material can be prepared by comminuting the sheet material to form randomly generated particles, and/or by cutting the sheet material to form particles of regular shape (e.g. in the form of circular, ovoid and/or polygonal shapes).

A further embodiment provides a cellular graft that comprises a filament comprised of an extracellular matrix material, and a population of cells attached to the filament. The filament can be a segment of a naturally-derived extracellular matrix sheet material isolated from an animal source and processed so as to retain endogenous growth factor(s), glycosaminoglycan(s) and/or proteoglycan(s).

Another embodiment provides a cellular graft that includes a cell growth substrate in the form of a filament, and a population of cells attached to the filament, where the cells include endothelial progenitor cells. This cellular graft can be introduced into tissue of a patient in a further embodiment of the invention which provides a method for vascularizing tissue of a patient.

Another embodiment provides a method for preparing a cellular graft. The method includes providing a first cell growth substrate sheet, and first applying a cellular composition to a surface of the first cell growth substrate sheet to form a first cell-seeded surface. After said first applying, the method includes stacking a second cell growth substrate sheet against said first cell-seeded surface. The method can also include second applying a cellular composition to a surface of the second cell growth substrate sheet.

Another embodiment provides a cellular graft that includes a first cell growth substrate sheet and a second cell growth substrate sheet stacked on the first sheet. The graft also includes a layer of seeded cells between the first sheet and the second sheet.

Another embodiment provides a device for preparing a cell-seeded graft. The devices includes an incubation chamber for receiving a cell growth substrate and an application device for applying a liquid cell suspension to the cell growth substrate, the application device comprising a plurality of cannulae for dispensing amounts of the suspension. The device can be configured to retract the plurality of cannulae while dispensing amounts of the suspension therefrom.

In still another embodiment, provided is a cell growth substrate composition that includes a particulate material comprising sheet-form cell growth substrate particles have a compact shape. In some forms, at least 25% of the sheet-form substrate particles, when considered in the plane of the sheet, have a first, maximum cross sectional dimension axis which is no more than about two times the length of a second cross sectional axis taken on a line perpendicular to and centered upon the maximum cross sectional dimension axis. The substrate particles can have a maximum cross sectional dimension in the range of about 20 microns to about 2000 microns. The substrate particles can be particles of a naturally-derived extracellular matrix sheet material isolated from an animal source and optionally processed so as to retain endogenous growth factor(s), glycosaminoglycan(s) and/or proteoglycan(s). Such particles of a naturally-derived extracellular matrix sheet material can be prepared for example by cutting the sheet material to form particles of a compact shape (e.g. in the form of circular, ovoid and/or polygonal shapes).

Another embodiment provides an extracellular matrix composition that includes a particulate extracellular matrix material comprising sheet-form extracellular matrix particles having a compact shape. At least 25% of the sheet-form extracellular matrix particles, when considered in the plane of the sheet, can have a first, maximum cross sectional dimension axis which is no more than about two times the length of a second cross sectional axis taken on a line perpendicular to and centered upon the maximum cross sectional dimension axis. The extracellular matrix particles can have a maximum cross sectional dimension in the range of about 20 microns to about 2000 microns. The extracellular matrix particles can be particles of a naturally-derived extracellular matrix sheet material isolated from an animal source and optionally processed so as to retain endogenous growth factor(s), glycosaminoglycan(s) and/or proteoglycan(s). Such particles of a naturally-derived extracellular matrix sheet material can be prepared for example by cutting the sheet material to form particles of a compact shape (e.g. in the form of circular, ovoid and/or polygonal shapes). The extracellular matrix composition can also include cells attached to the particles, with the cells in certain embodiments covering substantially the entire outer surface of the particles and/or forming a substantially confluent monolayer on the surface. The cells can include endothelial cells, endothelial progenitor cells, or a mixture thereof, and/or can be clonal. In some forms, the cells can consist of endothelial cells, endothelial progenitor cells, or a mixture thereof.

In another embodiment, provided is a cell growth substrate article that includes a cell growth substrate material and an encapsulating material encapsulating the cell growth substrate material and configured to direct flow of a fluid medium through the substrate material. The encapsulating material can define at least a first opening, and at least a second opening spaced from the first opening.

Another embodiment provides a cellular graft that includes a mixed population of cells derived from adipose tissue and including stem cells, endothelial progenitor cells, leukocytes, endothelial cells, and vascular smooth muscle cells. The cellular graft also includes a cell growth substrate that is comprised of an extracellular matrix material and/or that is in particulate form. The extracellular matrix material can include a retained bioactive component native to a source tissue for the extracellular matrix material. The retained bioactive component can be a growth factor(s), glycosaminoglycan(s) and/or proteoglycan(s). When used, a particulate cell growth substrate can comprise sheet-form particles. For these purposes, sheet form particles of a naturally-derived extracellular matrix sheet material can be prepared for example by cutting the sheet material to form particles, for example of a compact shape (e.g. in the form of circular, ovoid and/or polygonal shapes).

In a further embodiment, provided is a cellular graft that includes a population of endothelial progenitor cells and a particulate cell growth substrate. The particulate cell growth substrate can include sheet-form particles and/or can include an extracellular matrix material. Extracellular matrix particles for these purposes can be particles of a naturally-derived extracellular matrix sheet material isolated from an animal source and optionally processed so as to retain endogenous growth factor(s), glycosaminoglycan(s) and/or proteoglycan(s). Such particles of a naturally-derived extracellular matrix sheet material can be prepared for example by cutting the sheet material to form particles of a compact shape (e.g. in the form of circular, ovoid and/or polygonal shapes), or can be fragments of the sheet material, e.g. generated by randomly comminuting the sheet material.

Another embodiment provides a system for seeding a matrix with cells. The system includes a chamber for combining cells with a cell growth substrate to be seeded with the cells. The system also includes a mechanism for assessing adherence of the cells to the substrate. The mechanism for assessing can comprise a cell counter. Related methods for seeding a matrix comprise the steps of combining cells with a cell growth substrate to be seeded with the cells, and assessing adherence of the cells to the substrate. In treatment methods, the methods can also include administering the substrate, seeded with adhered cells, to a patient, including a human patient.

Additional embodiments of the invention as well as features and advantages thereof will be apparent from the further descriptions herein.

DETAILED DESCRIPTION

Figure 1:
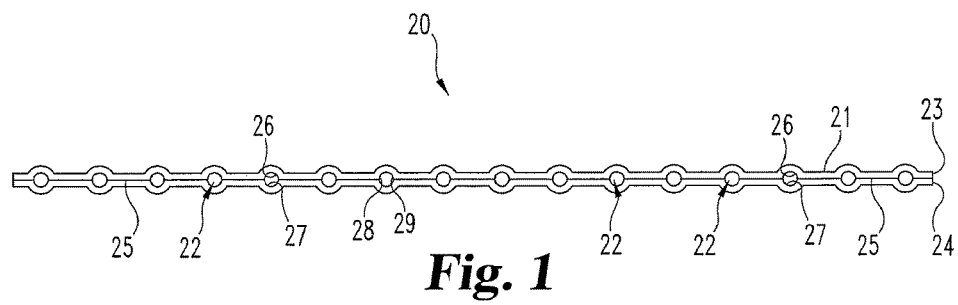
FIG. 1 provides a side view of one embodiment of a cell growth substrate of the invention.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As disclosed above, aspects of the present invention relate to methods, materials and systems for combining cells with substrate materials to prepare compositions that can be used in certain embodiments as medical implants for patients.

Cell Growth Substrates Having Defined Internal Passages

Referring now to FIGS. 1-8, shown are various embodiments of cell growth substrate constructs that are particularly useful for combination with cellular compositions to form cell-containing graft materials.

In particular, FIG. 1 provides a side view of a matrix substrate 20. Substrate 20 includes a substrate body 21 preferably comprised of a porous matrix material suitable for supporting cellular growth. Substrate body 21 includes internally defined passages 22 extending into an interior region of the substrate body 21. In the depicted embodiment 20, substrate body 21 includes a first sheet 23 connected to a second sheet 24 in such a fashion as to define passages 22 between sheet 23 and sheet 24. Sheet 23 and sheet 24 are connected to one another along a connected region 25 in areas surrounding passages 22. Connected region 25 may, for example, be a bonded, fused, glued, cross-linked, sutured, or other arrangement establishing a close connection between the opposed faces of sheet 23 and sheet 24. Tubular passages 22 thus include a passage wall having a portion 26 defined by a face of sheet 23 and a portion 27 defined by an opposed face of sheet 24. In the illustrated embodiment, regions 26 and 27 are generally rounded, providing a substantially circular or ovate cross section to passages 22. It will be understood that other arrangements are also suitable, including passages having polygonal or irregular cross sectional shapes. Connected region 25 has terminus regions 28 and 29 at the lumens of passages 22. Terminus regions 28 and 29 can thus occur as seams along the walls of passages 22.

To prepare substrate 20, a passage-forming element or elements can be placed between sheet 23 and sheet 24, and these sheets can then be connected to one another in connection regions 25 thus sandwiching the passage-forming element or elements between the sheets. As noted above, this connection can be by bonding, fusing, gluing, or otherwise. Where an opening of passage 22 to the outermost edge of substrate 20 is desired, the passage-forming element or elements can extend to or beyond the outermost edges of sheets 23 and 24 as they are layered against one another, thus providing such openings in the finished product. In such preparative methods, the passage-forming element or elements can be rods, bars, comb structures, wires, tubes, or any other element suitable for maintaining space between the sheets 23 and 24 for providing a passage in the completed product. In embodiments in which the passage-forming element or elements will be removed after formation of the connected regions 25, it is desired that the passage-forming element(s) have an exterior surface that will sufficiently avoid sticking or bonding to the opposed faces of sheets 23 and 24 such that the passage-forming element(s) can be removed after formation of the connected regions 25 to leave passages 22 intact.

Figure 2:
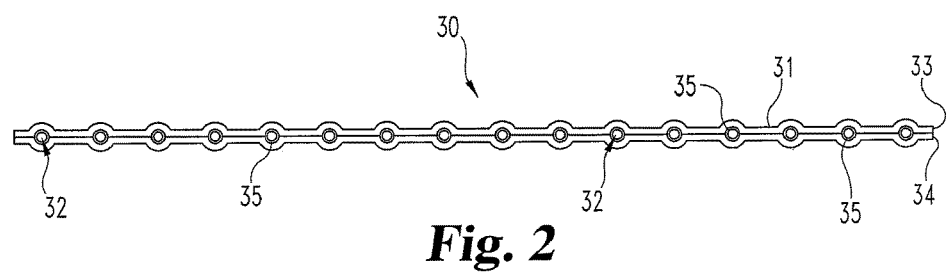
FIG. 2 provides a side view of another embodiment of a cell growth substrate of the invention.

In certain embodiments, the passage-forming element(s), or at least portions thereof, will be left resident within the finished product. Referring now to FIG. 2, one such embodiment is shown. Substrate 30 includes the same features as matrix 20 and as a general matter can be constructed in the same fashion. Thus, substrate 30 includes a body 31, passages 32 to interior regions of the body 31, and sheets 33 and 34 connected to one another. Additionally, substrate 30 includes resident tubular elements 35 received between sheets 33 and 34. Tubular elements 35 can be made from biocompatible polymers or other suitable materials and can remain in substrate 30 for implantation into a patient. Tubular elements 35 can comprise persistent polymers (non-bioresorbable) or bioresorbable polymers. In certain embodiments, tubular elements 35 comprise bioresorbable polymers and can be completely resorbed after implantation in a patient. In the manufacture of substrate 30, tubular elements 35 can be placed between sheets 33 and 34, and then the sheets can be connected as discussed above in connection with substrate 20 (FIG. 1). Alternatively, a device such as substrate 20 can first be prepared, and tubular elements can thereafter be inserted into the passages 22. Tubular elements 35 can include porous walls, or holes or perforations in their walls, to allow the transmission of a flowable cell suspension through the walls of tubular elements 35 and into surrounding regions of the graft body 31. In certain forms, the tubular elements 35 are constructed of material that is less absorptive to an aqueous cellular suspension than the material of the body 31, and/or remains more rigid than the material of body 31 when wet so as to retain an open passage, and thus can serve to better transmit a flow of an aqueous cellular suspension along passages 32 to reach interior regions of the substrate 31. The porosity of or perforations in tubular elements 35 can be controlled to optimize wetting and cell seeding of the substrate 31 upon inputting a flow of an aqueous cellular suspension into passages 32.

Figure 3:
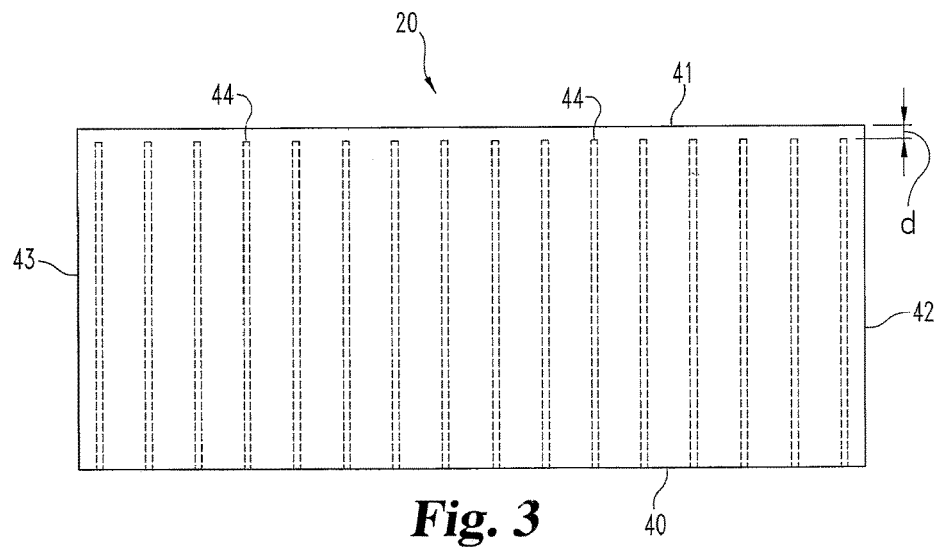
FIG. 3 provides a top view of the substrate of FIG. 1.

With reference now to FIG. 3, shown is a top view of the substrate device 20 of FIG. 1. Passages 22 are shown in phantom (dotted lines). Substrate 20 as depicted is a generally rectangular structure including a first pair of generally parallel sides 40 and 41, and a second pair of generally parallel sides 42 and 43 perpendicular thereto. Passages 22 have an opening exposed at side 40 of substrate 20. Passages 22 in the depicted embodiment are blind holes, and have a terminus 44 within the interior of body 21, spaced a distance "d" from side 41 of body 21. In this fashion, fluid compositions such as aqueous cellular suspensions can be passed into passages 22 from side 40, and will not be carried all the way to the opposite side 41 by the passages 22. This can provide an enhanced ability to generate fluid pressure within passages 22 to more rapidly disperse a cell suspension and/or another fluid, such as a substrate preconditioning medium, into adjacent regions of body 21. In certain modes of use, the blind hole passages 22 can be subjected to fluid pressure by fluid introduced through the openings to passages 22 at side 40, to drive the fluid and dissolved or suspended (e.g. cells) materials into and through the volume of body 21.

Figure 4:
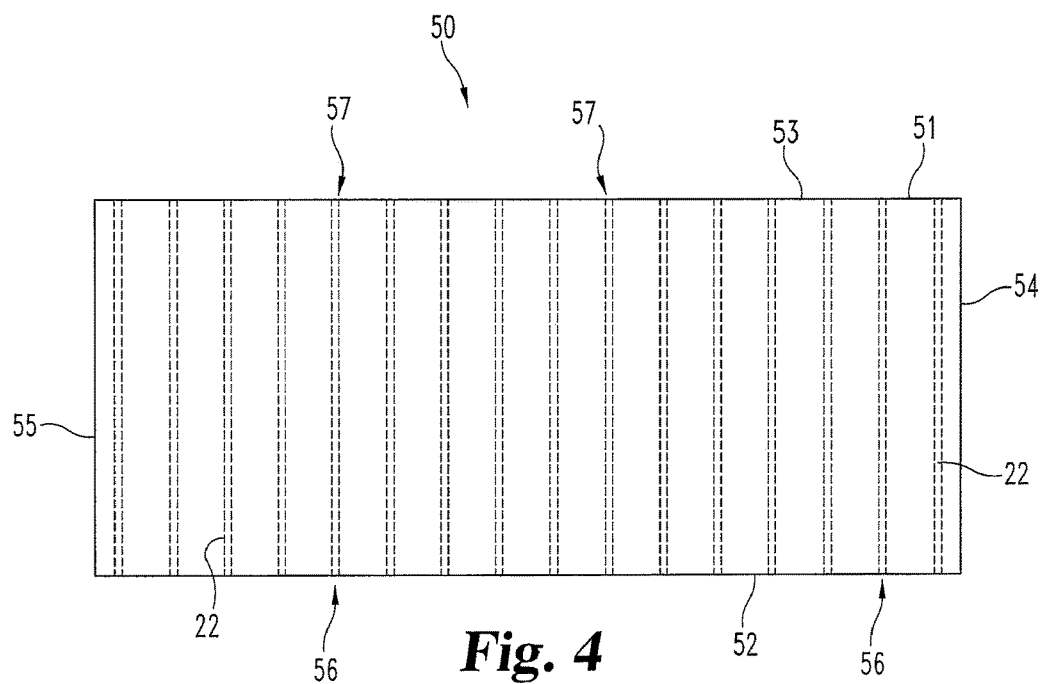
FIG. 4 shows a top view of an alternative cell growth substrate of the invention.

With reference to FIGS. 4-8, shown are alternative embodiments of substrate devices defining internal passages. Specifically with reference to FIG. 4, shown is a cell growth substrate 50 having features similar to those of substrate 20 of FIGS. 1 and 3, except having passages that extend completely from a first perimeter to a second perimeter of the substrate. In particular, substrate 50 includes a body 51 of generally rectangular shape having a first side 52, a second side 53 generally parallel with side 52, a third side 54, and a fourth side 55 generally parallel with side 54. Substrate 50 includes a plurality of passages 22 extending through the material of body 51. The passages 22 have a first group of openings 56 occurring on side 52 of substrate 50, and second group of openings 57 occurring on side 53 of substrate 50 opposite to side 52. In this fashion, passages 22 present openings 56 and 57 at spaced locations on substrate body 51 and in the illustrated embodiment on opposed sides 52 and 53. A flowable composition including cells can be passed through passages 22 from openings 56 to openings 57 to allow the cells to penetrate, contact and adhere to the material of body 51, so as to populate the substrate 50 with cells.

Figure 5:
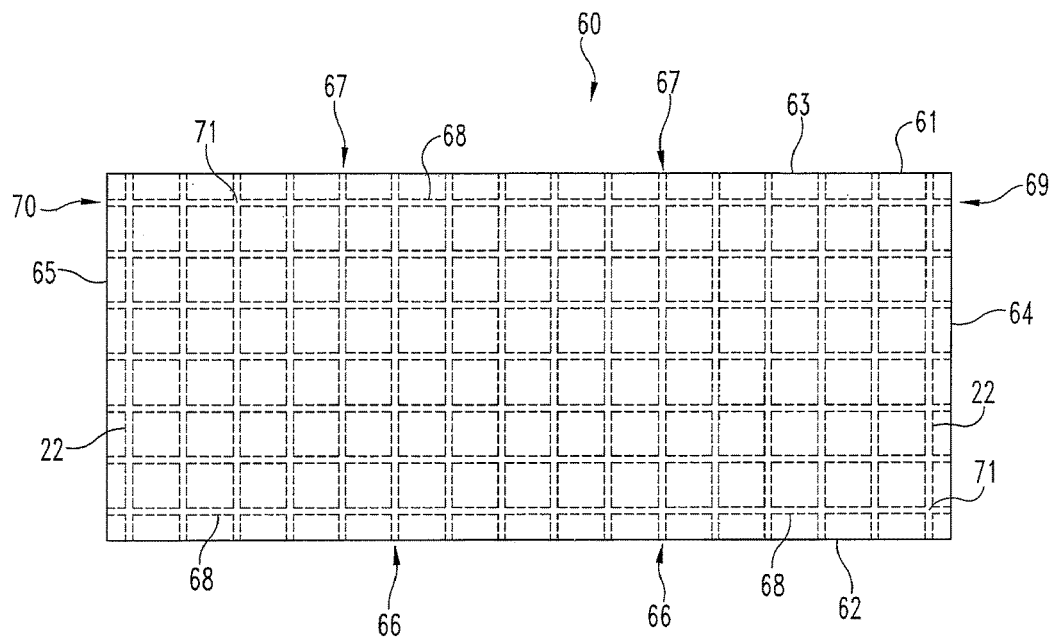
FIG. 5 shows a top view of a further embodiment of a cell growth substrate.

With reference to FIG. 5 shown is a cell growth substrate 60 similar to substrate 50 of FIG. 4, except having first and second sets of passages which are transverse to one another. Thus, substrate 60 includes a substrate body 61 having a first side 62, a second side 63, a third side 64, and a fourth side 65. Substrate 60 includes a first plurality of passages 22 having openings 66 at side 62 and opposed openings 67 at side 63 of body 61. Substrate 60 includes a second plurality of passages 68 which pass through the body 61 in a direction transverse to that of passages 22, and in the illustrated embodiment substantially perpendicularly to the direction of passages 22. Passages 68 include openings 69 occurring in side 64, and opposed openings 70 occurring in side 65. In certain embodiments, passages 68 are fluidly coupled to and intersect passages 22 at passage intersections 71 distributed throughout body 61. In use, substrate 60 can be populated with cells by flowing cellular compositions through passages 22 and through passages 68. In this regard, fluid cellular compositions can be passed through passages 22 and 68 simultaneously, or at different times, or using a combination of these during a cell populating operation. In embodiments in which passages 22 and 68 intersect one another and are thus fluidly coupled, the simultaneous passage of cellular compositions or other fluids simultaneously through passages 22 and 68 can create fluid flow conditions at intersections 71, such as turbulence, eddies, or at least a partial redirection of net flow along a vector that is aligned with neither passages 22 nor 68, so as to facilitate driving the fluid out of the passages and into the surrounding volumes of material making up substrate body 61. This can provide a more rapid or efficient distribution of cells or other substances throughout the volume of substrate body 61.

Figure 6:
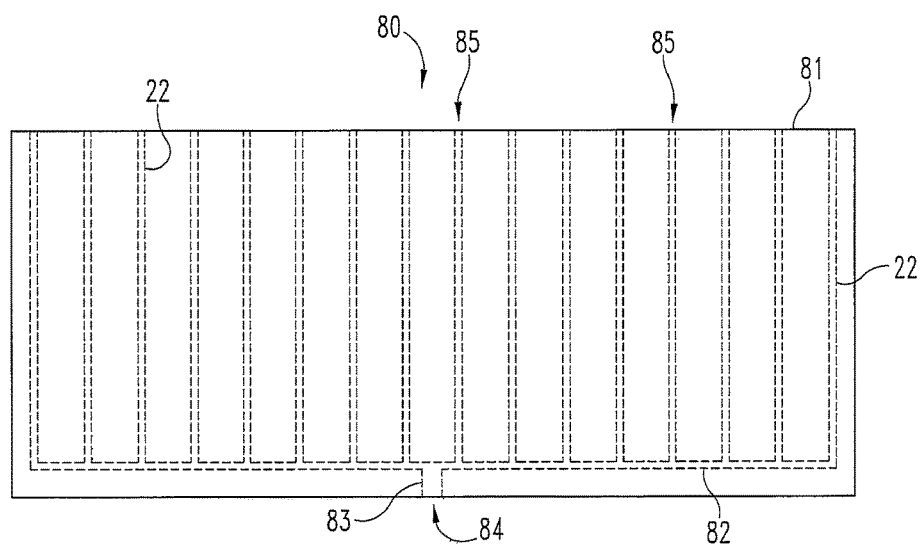
FIG. 6 shows a top view of another embodiment of a cell growth substrate, having a manifold feed.

Referring to FIG. 6, shown is a cell growth substrate 80 having a plurality of passages 22 fed by a common manifold structure. Specifically, substrate 80 includes a body 81 having a plurality of passages 22 extending therethrough. A common feed passage 82 fluidly couples to a plurality of passages 22. Common feed passage 82 is in turn fluidly coupled to input passage 83 having an opening 84 to the exterior of body 81. Passages 22 each have an opening 85 to the exterior of body 81. In use, a fluid such as a cellular composition can be passed into input passage 83 through opening 84, whereupon the fluid composition passes into common passage 82 which in turn distributes the fluid composition into and through passages 22, exiting via openings 85. In this manner, a fluid cellular or other composition can be circulated and potentially recirculated through substrate 80 to populate the substrate with cells. As with the other embodiments described herein, to accomplish this, passages 22 and potentially also passages 82 and 83 can be permeable to the composition to allow escape into the adjacent volumes of body 81.

Figure 7:
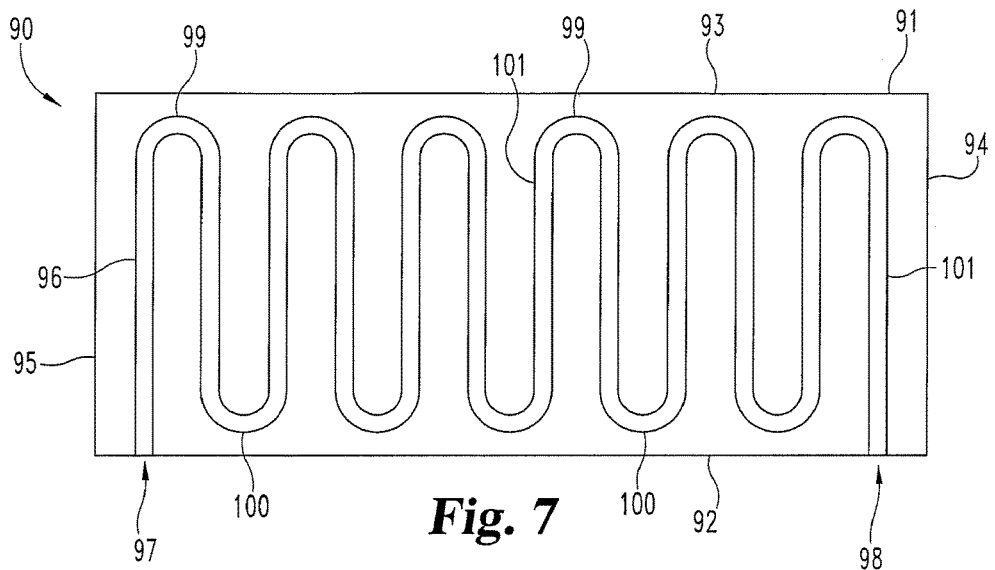
FIG. 7 shows a top view of another embodiment of a cell growth substrate.

Referring now to FIG. 7, shown is another cell growth substrate 90. Substrate 90 includes a body 91 and first, second, third, and fourth sides 92, 93, 94, and 95, respectively. Body 91 includes a tortuous passage 96 extending through the material of body 91 and having a first external opening 97 and a second external opening 98 spaced therefrom. In the illustrated embodiment, tortuous internal passage 96 includes a first plurality of bends 99 occurring opposite a second plurality of bends 100, with the bends 99 and 100 situated in opposed directions. Generally straight passage segments 101 interconnect bends 99 and 100. In this fashion, tortuous passage 96 takes on a generally repeating sinusoidal wave shape as it traverses from opening 97 to opening 98. Cell-containing fluid can be circulated from opening 97 through the tortuous passage 96 and to opening 98, during which cells and fluid escape passage 96 to provide cell seeding through the volume of substrate 91.

Figure 8:
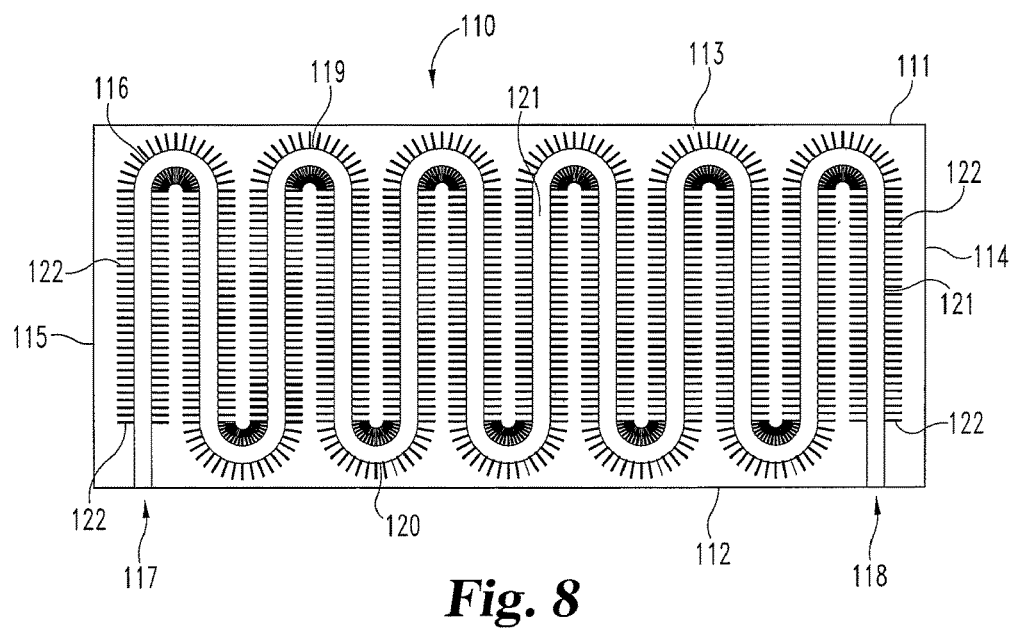
FIG. 8 provides a top view of another embodiment of a cell growth substrate, having larger primary channels and smaller secondary channels within the substrate.

Referring now to FIG. 8, shown is a cell growth substrate 110 sharing many features in common with substrate 90 discussed above, which are correspondingly numbered. Substrate 110, however, also includes a plurality of secondary passages 122 fluidly coupled to and leading from primary passage 116, with the secondary passages having diameters or cross sectional areas smaller than tortuous passage 116. Secondary passages 122 can thus receive flow of cellular fluid passed through primary passage 116 and help to distribute the fluid and accompanying cells throughout the substrate body 111.

It will be understood that in additional embodiments of the cell growth substrates depicted in FIGS. 1 and 3-8, separate tubular elements can be received within portions of or all of the defined internal passages, as discussed above in conjunction with FIG. 2. Additionally, in preferred embodiments, sheets (e.g. 23 and 24) used to prepare the illustrated substrates can be comprised of decellularized ECM tissue sheets, desirably retaining native (endogenous) bioactive component(s), as described hereinafter. As well, the bodies of the substrates illustrated in FIGS. 1-8 can be comprised or constituted of a porous sponge or foam matrix, which can be formed for example by casting a matrix-forming material, e.g. any of those described herein, around the passage and then be removed or left resident in the finished product to contribute to the passage, as discussed above.

Cell/Substrate Processing Systems and Methods

Figure 9:
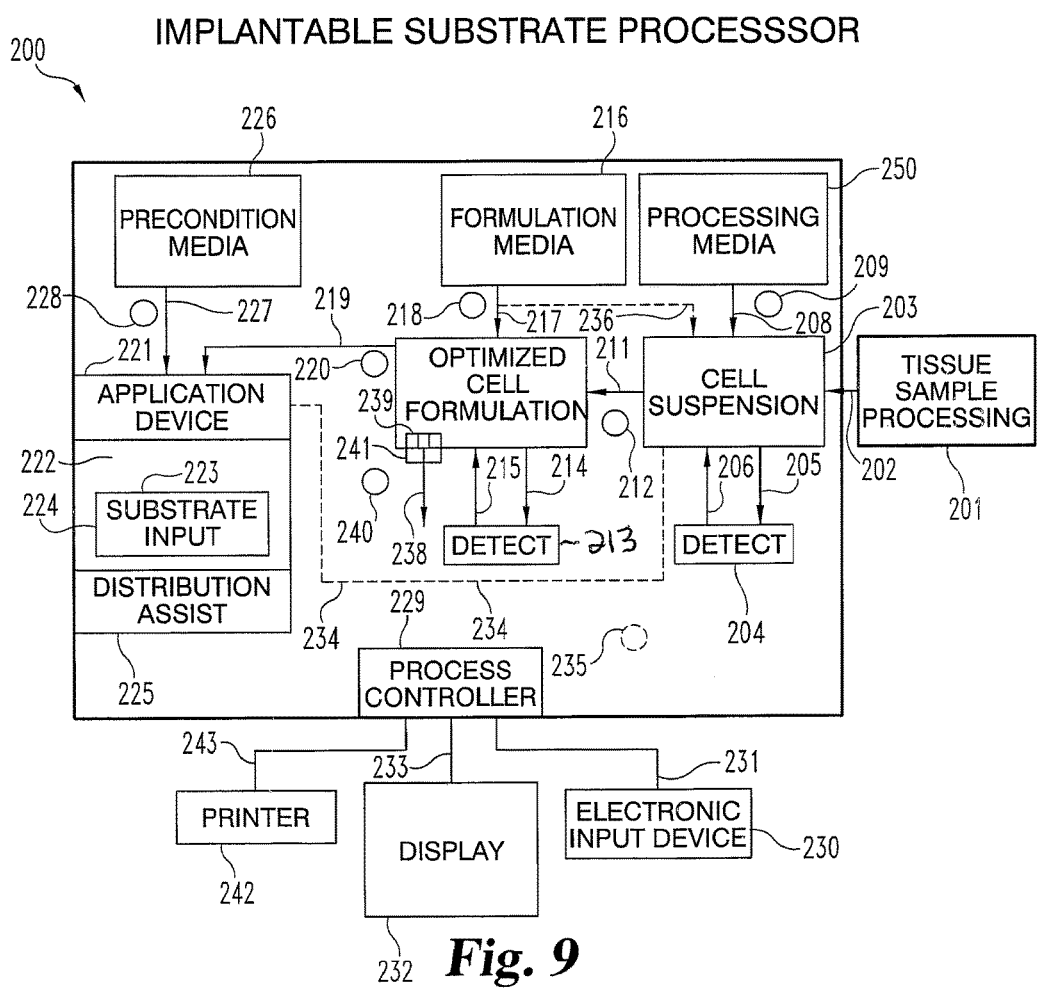
FIG. 9 provides a schematic diagram of one embodiment of a system for applying a cellular composition to a cell growth substrate.

In additional aspects of the invention, provided are devices for the automated seeding of substrates with cells. FIG. 9 provides a schematic diagram of one embodiment of an automated cell seeding system 200. System 200 can optionally include a raw tissue processing module 201 that processes raw or early-stage tissue samples to provide an output of a single cell suspension derived from the tissue samples. Processing module 201 can thus operate to perform one or more functions common to this purpose, including for example physical disruption of tissue (e.g. maceration), enzymatic (e.g. collagenase, trypsin) or other chemical disassociation of tissue, and/or washing of tissue or cellular components with saline or other suitable wash media. Tissue processing module 201 can also perform cell separation or concentration steps including for example immunochemical selection of specific types or groups of cells, fractionation, filtration, sedimentation, or other similar operations. Module 201 may also include features to expand cell populations, for example providing growth substrates or growth media and suitable incubation conditions for expanding cell number. Illustrative systems for tissue processing to output cell suspensions are disclosed in US Patent Publication No. US2005/0025755, published Feb. 3, 2005, International Publication No. WO2007/009036, published Jan. 18, 2007, US Patent Application Publication No. US2008/0014181, published Jan. 17, 2008, and US Patent Application Publication No. US2006/0141623, published Jul. 29, 2006. These publications are each hereby incorporated herein by reference in their entirety, for their teaching of tissue processing methods and equipment for achieving single cell suspensions suitable for use in module 201 of system 200.

The cell suspension output of module 201 is transferred via conduit 202 to cell suspension chamber 203. A device 204 for detecting at least one condition of the cell suspension is provided, to provide input for potential adjustment of the cell suspension prior to application to a substrate and/or for optimizing parameters for application of the suspension to a substrate. For example, device 204 may be operative to determine the concentration of cells in the cell suspension in chamber 203 and is operably associated with chamber 203. By way of non-limiting example, device 204 can be a cell counting device such as a Coulter counter, which arrives at a cell count value based upon electrical resistance changes of a liquid filled channel during passage of the cells through the channel. This resistance change can be sensed as electric current or voltage pulses, which can be correlated to the concentration of the cells within the cell suspension. The device 204 may also be a device that utilizes light scattering, such as forward light scattering using a laser, to calculate a cell concentration value. The device 204 may also be a device that uses flow cytometry to determine the cell concentration within the cell suspension. Other means for measuring cell concentration will be apparent to those skilled in the art, and it will be appreciated that the particular means for measuring cell concentration is not critical to the presently disclosed systems and methods.

To facilitate the cell concentration analysis, device 204 can draw off a sample of the cell suspension via conduit 205, for analysis. Optionally, device 204 can return the cell sample to the chamber 203 after the analysis via conduit 206, unless this would cause unwanted contamination of the cell suspension within chamber 203, in which case the drawn sample can be discarded via a waste line (not shown). Device 204 and/or the chamber 203 may include appropriate valves and optional pumps (not shown) for the movement of cell samples through the conduits 205, 206 as will be apparent to those skilled in the art. Such valves and/or pumps may be under the control of process controller 229 as discussed in greater detail hereinbelow.

System 200 can also include a processing media unit 207 fluidly coupled to chamber 203 via conduit 208. As with all other conduits in which fluid media are to be transferred in system 200, conduit 208 can be associated with optional valves (not shown) and a pump 209 operable to power the transfer of fluid from media unit 207 to chamber 203. It will be understood that pump 209 can be provided by a shared pump duty in which a single pump powers fluid transfer amongst some or all of the various chambers or other components of system 200. Thus, although several separate pumps are discussed in conjunction with system 200, it will be understood that these pump operations could be shared or separate, or combinations thereof, within the operation of system 200. Such valves and/or pump may be under the control of process controller 229 as discussed in greater detail hereinbelow. Processing media unit 207 can include one or more chambers containing, or into which can be charged, any of a variety of media for treating or processing the cell suspension composition output from the module 201. These media could include, for example, wash media, cell culture media, or other materials for readying the cells for application to the cell growth substrate, including for example differing media for differing stages of a cell expansion phase.

System 200 also includes an optimized cell formulation chamber 210 fluidly communicating with first cell suspension chamber 203 via conduit 211, optional valves (not shown), and associated pump 212. Such valves and/or pump 212 may be under the control of process controller 229 as discussed in greater detail hereinbelow. Thus, after any initial processing in chamber 203, the cell suspension composition can be transferred to the chamber 210 for further processing via the operation of pump 212 to transfer the suspension through conduit 211. A device 213 for determining the concentration of cells in the optimized cell formulation within chamber 210 is provided. Device 213 can be of similar design to device 204 discussed above. A conduit 214 can serve in the transfer of a sample of the cell suspension composition from chamber 210 to the device 213 for analysis. A conduit 215 can optionally be provided for returning the sample to the chamber 210 should that be appropriate. As above, alternatively, the sample can be discarded after the analysis via a waste line.

A formulation media unit 216 is fluidly coupled to chamber 210 via conduit 217. Transfer of materials from one or more chambers of unit 216 to the chamber 210 can be facilitated by optional valves (not shown) and pump 218. Such valves and/or pump 218 may be under the control of process controller 229 as discussed in greater detail hereinbelow. The formulation media unit 216 can contain materials that are to be combined with the cell suspension and that are physiologically acceptable for administration to patients. The formulation media may for example include saline, cell culture media, drugs such as antibiotics, substances designed to illicit a specific cellular response such as differentiation or quiescence, or other materials. In one use, device 213 is used to determine the cell concentration of the cell suspension within chamber 210. If the concentration of cells is higher than that desired for application to a cell growth substrate, formulation media can be added from chamber 216 to dilute the cell suspension to achieve the desired cell concentration. The volume of formulation media to add can be calculated based upon the overall volume of the composition within chamber 210 and the cell concentration determined by device 213. Beneficial cell concentration values for the optimized cell formulation in chamber 210, to be applied to the cell growth substrate, can range from about $10^5$ to about $10^8$ cells per ml, although other concentrations can be used. In alternative situations in which the cell concentration is lower than desired, then chamber 210 can be operably associated with means for increasing the cell concentration, e.g. by removing amounts of media. In one embodiment, an outlet 238 from chamber 210 can be provided with a filter 239 having a pore size selected to prevent passage of the cells but allow passage of the fluid media suspending the cells. Optional valves (not shown) and a pump 240 can be provided to drive or pull amounts of the cell suspension against this filter to selectively remove amounts of the fluid media from chamber 210 and thus concentrate the cell suspension within chamber 210. A vibration device 241 can be provided if needed, to impart vibration to the filter to resist clogging of the filter with cells during operation. Additionally or alternatively, the system can be configured with appropriate pump(s) and/or valves to direct a reverse flow of liquid through the filter to clean the same in a back flush mode. Such operations and any attendant valves, pump 240 and/or vibration device 241 may be under the control of process controller 229 as discussed in greater detail hereinbelow. Materials removed from chamber 210 via outlet 238 can for example go to a waste unit "W". If desired, waste unit W can also be fluidly coupled to chamber 203 or other fluid sources in system 200, to receive waste therefrom into a single waste chamber or separate waste chambers. After upward or downward adjustment of the cell concentration within chamber 210 as a result of a prior-initiated concentration measurement or otherwise as a result of the introduction or withdrawal of media from chamber 210, an additional sample can be drawn off into device 213 and assessed to confirm that the cell suspension is within a desired cell concentration range. Additional adjustments can be made as necessary to achieve the desired cell concentration. After the cell suspension is confirmed to have the desired cell concentration, the cell suspension can be transferred from chamber 210 to an application device 221 via conduit 219, using optional valves (not shown) and powered by pump 220. Such valves and/or pump 220 may be under the control of process controller 229 as discussed in greater detail hereinbelow.

Application device 221 can be any of a variety of devices for applying the cell suspension composition to a cell growth substrate 223 received within seeding chamber 222. Application device 221 may be stationary during operation, or may be movable during operation to apply material across a broader area or volume that would be possible if it were stationary. Application device 221 may be under the control of process controller 229 as discussed in greater detail hereinbelow. Application device 221 may in one embodiment be a spray device, for example a spray nozzle or a jet spray apparatus similar to that found in ink jet printers. Such spray devices can be arranged to apply the cell suspension composition to the substrate by spraying the composition against the substrate, either from a stationary position or upon movement in one, two or three dimensions. In another embodiment, the application device 221 can be a cannulated device having at least one cannula and preferably a plurality of cannulae for application of the cellular composition to the surface of and/or within the cell growth substrate 223 from a stationary position or during movement in one, two or three dimensions. Some embodiments incorporate a cannulated application device 221 that has one cannula or a plurality of cannulae inserted into the substrate 223 during application of the cellular composition, for example by expressing the cellular composition from the cannula(e) during a pull back operation beginning with the cannula(e) inserted at a distal position within the volume of the substrate 223. In a specific embodiment, such an application device includes a linear or other array of needles for application of the cell composition to the substrate 223. Still other application modes will be apparent to those of ordinary skill in the art.

Application device 221 desirably applies the cellular composition to the substrate substantially evenly to the surface of the substrate or through the volume of the substrate. However, in other embodiments, application device 221 may selectively seed certain portions of the substrate, and thus the application device 221 can be configured to apply the cellular composition to specific regions of the substrate 223 while leaving other regions of the substrate free of the cellular composition. Combinations of different types of application devices 221 can be incorporated into system 200, for example wherein the system includes both a spray application device and a cannulated application device.

In particular embodiments of the invention, system 200 has an application device 221 configured to seed cells onto and/or into cell growth substrates that define internal passages for receiving flow of cellular compositions, for example substrates such as those depicted in FIGS. 1-8. Application device 221 in such embodiments desirably includes at least one cannula and preferably a plurality of cannulae. In certain embodiments, the cannula(e) are fluidly coupled to the defined passages in the substrate (e.g. passages 22, 68, 83, 84, 96, and/or 116 of FIGS. 1-8) and operable to pass amounts of the cellular composition into the passages. In additional embodiments, a cannula is provided on the application device 221 for each opening of a passage to the exterior of the cell growth substrate, wherein the cannulae correspond to and register with such openings. In application devices 221 that are static during application of the cellular composition, the cannula(e) can direct the cellular composition into the passages under pressure, which will lead to flow of the cellular composition through the passages, out of the sidewalls of the passages, and into the surrounding volume of material of the substrate. With cell growth substrates that include individual passages that have openings at spaced locations on the substrate, for example passages 22 of the substrate of FIG. 4 with spaced openings 56 and 57, passages 22 and 68 of the substrate of FIG. 5 with spaced opening pairs 66,67 and 69,70, respectively, passages 83, 84 and 22 of the substrate of FIG. 6 with spaced openings 84 and 85, and passages 96 and 116 of the substrates of FIGS. 7 and 8 with spaced opening pairs 97,98 and 117,118, respectively, application device 221 can have a cannula fluidly connected to each opening. Such an application device 221 can for example be operated in a flow-through mode, an opposed flow mode, or a combination thereof. In a flow-through mode, input cannula(e) force the cellular composition into a first opening to a passage and output cannula(e) receive fluid that traverses the passage, having deposited at least a portion of the cells of the input composition in the cell growth substrate. In an opposed flow mode, input cannula(e) force the cellular composition into both the first opening and the second opening to a passage, wherein the respective input flows to the passage oppose one another. This can create pressure within the passage and thus drive cellular fluid out of the passage and into the surrounding volumes of substrate material, facilitating a more even seeding operation.

A flow-through mode as noted above can involve only a single passage of the cellular composition through the substrate, but in advantageous embodiments will be conducted so as to pass the material received in the output cannula(e) back through the substrate passage(s) at least one time to deposit additional cells, which can be accomplished for example by collecting the output fluids and reversing the direction of flow through the passages, and/or by providing a recirculation loop in which the output fluids are directed again to the same input cannula(e) and back through the substrate passage(s) to the output cannula(e). In many embodiments, the original output fluids, containing unseeded cells, will be passed back through the substrate passages a plurality of times to seed a higher percentage of the original cells in the cellular composition into the substrate.

Figure 9A:
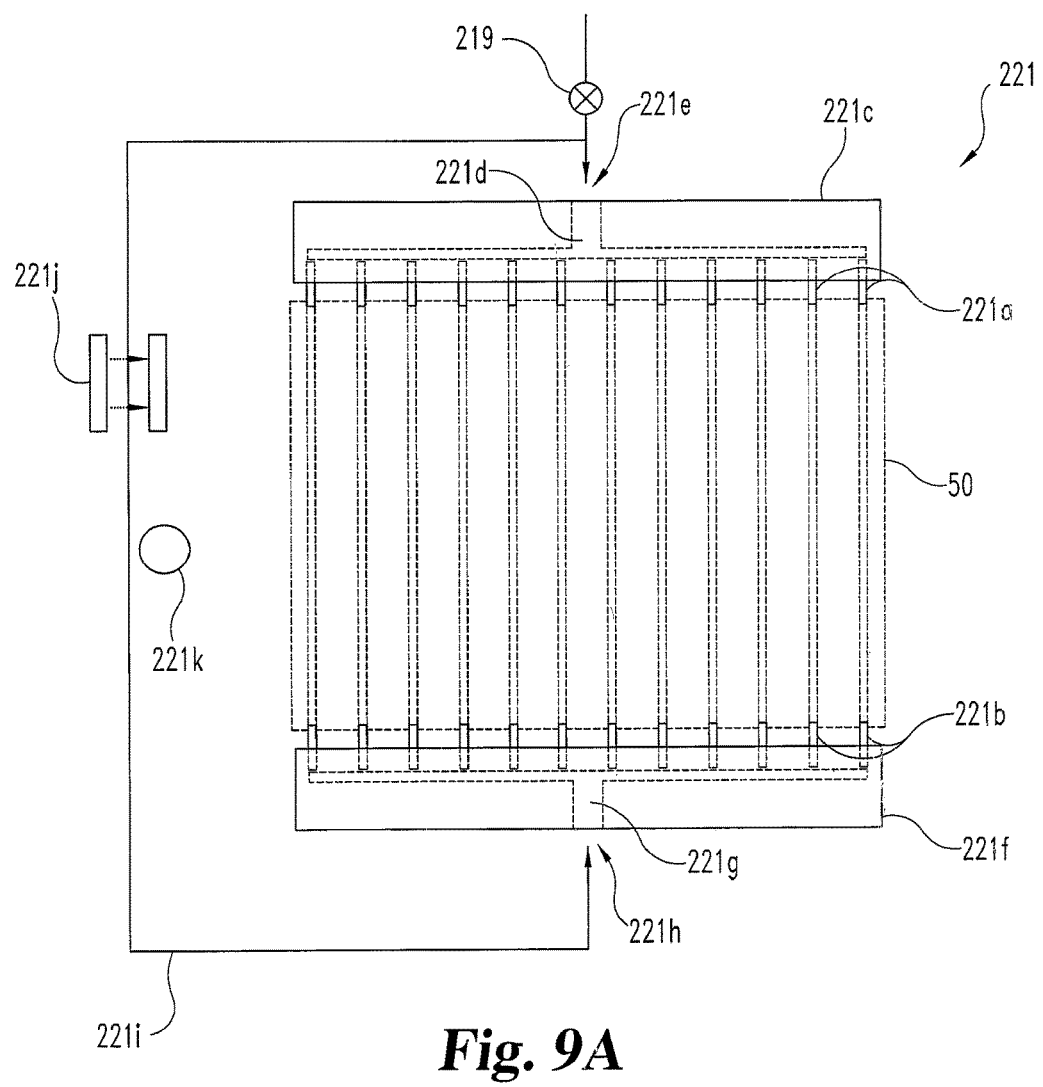
FIG. 9A illustrates one embodiment of certain subcomponents of the system of FIG. 9.

In this regard, with reference to FIG. 9A, in conjunction with FIG. 9, shown is one embodiment of a circulation loop application device 221 useful for seeding an internally-plumbed cell growth substrate 50 such as that shown in FIG. 4. Application device 221 has a plurality of input cannulae 221a and a plurality of output cannulae 221b, with the input cannulae 221a fluidly coupled to openings 56 of substrate 50 and the output cannulae 221b fluidly coupled to openings 57 of substrate 50. Input cannulae 221a are mounted in input manifold 221c, which defines an internal input manifold passage 221d having an opening 221e, with the manifold passage 221d fluidly coupled to and feeding each of input cannulae 221a. Opening 221e is fluidly connected to conduit 219 (FIG. 9) which provides a feed of the cellular composition from chamber 210. Output cannulae 221b are mounted in output manifold 221f, which defines an internal output manifold passage 221g having an output opening 221h, with the output cannulae 221b fluidly coupled to and feeding output manifold passage 221g. A circulation loop 221i is provided fluidly connecting input opening 221e of input manifold 221c and output opening 221h of output manifold 221f. A cell counter 221j, such as one using the Coulter principle, light scattering or flow cytometry to provide a calculated cell concentration, can be fluidly coupled to circulation loop 221i. Cell counter 221j can determine cell concentration in the fluid circulating in loop 221 in-line or by drawing and assessing a sample, as noted in the discussions above. Optional valves (not shown) and a pump 221k is provided to drive circulation in the application device 221 for seeding the substrate 50. Such cell counter 221j, valves, and/or pump 221k may be under the control of process controller 229 as discussed in greater detail hereinbelow.

In use, a cellular composition fed to the circulation loop of application device 221 from conduit 219 in a batch operation, continuously, or intermittently, is repeatedly circulated through input manifold 221c, input cannulae 221a substrate 50, output cannulae 221b, output manifold 221f and circulation loop 221i. During this operation, cells will be seeded into substrate 50, and some cells will remain in the circulating fluid. Cell counter 221j can be used to continuously or periodically determine the cell concentration of the fluid circulating in circulation loop 221i. Seeding of an acceptable percentage of the originally-provided cells into substrate 50 will be determined by system 200 and/or signaled to a user, for example by use of process controller 229 described in greater detail hereinbelow, at a point in time when the cell concentration detected by cell counter 221j reaches a desired or predetermined low value. Circulation within application device 221 can thereafter be terminated, and substrate 50 can be prepared for administration to the patient immediately, or after a further incubation or culture period.

Figure 9B:
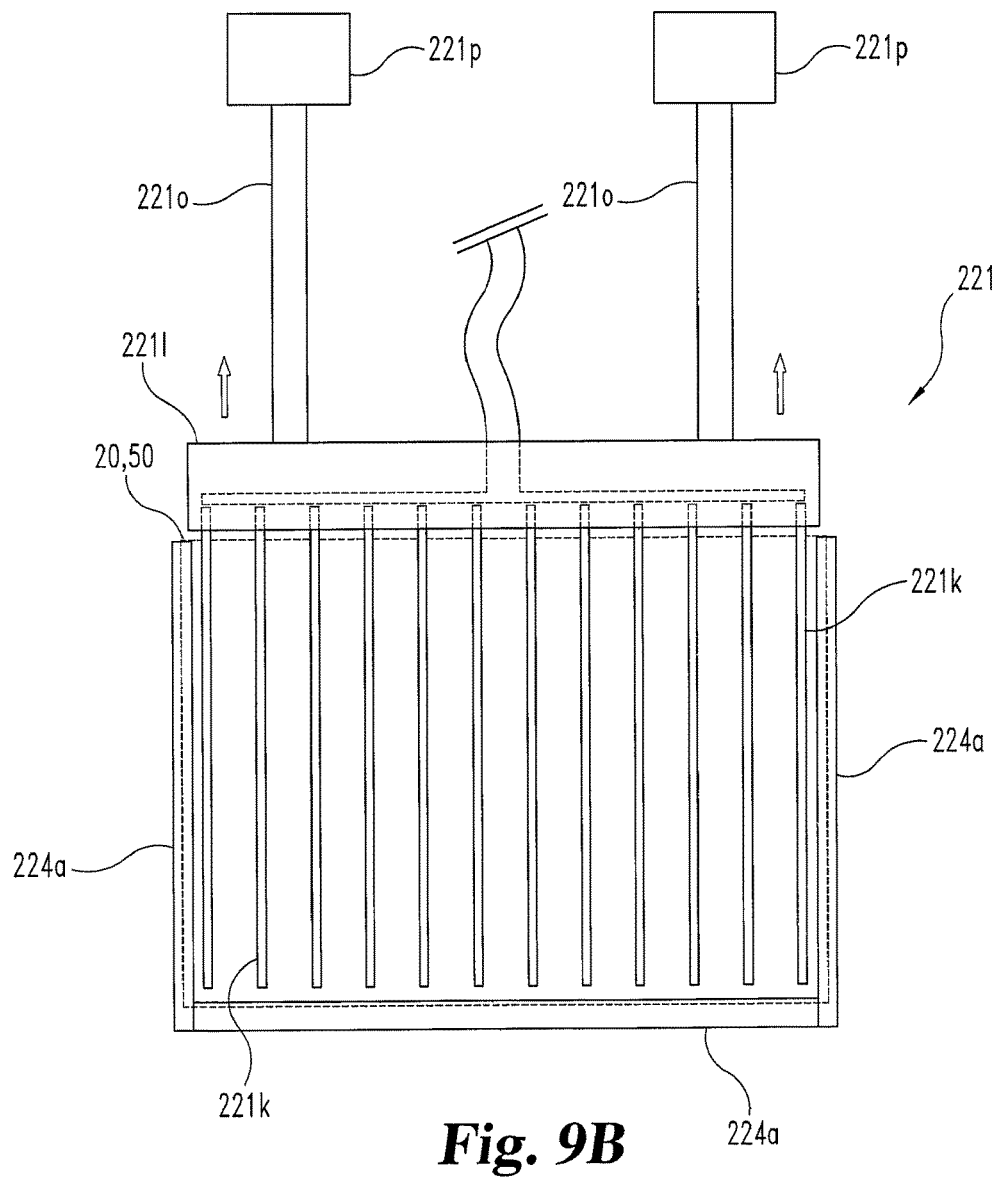
FIG. 9B illustrates another embodiment of certain subcomponents of the system of FIG. 9.

As disclosed above, in other embodiments, application device 221 is configured to move during application of the cellular composition to the substrate. With reference to FIG. 9B, in conjunction with FIG. 9, shown is one such application device 221, useful for applying a cellular composition to a pre-plumbed cell growth substrate such as substrate 20 of FIG. 3 or substrate 50 of FIG. 4 (shown in phantom, dotted lines of FIG. 9B). Application device 221 of FIG. 9B includes a plurality of cannulae 221k mounted to an input manifold carriage 221l. Input manifold carriage 221l defines an internal manifold passage 221m having an input opening 221n, with manifold passage 221 fluidly coupled to and feeding cannulae 221k. Input opening 221n is fluidly connected to conduit 219 of system 200, which feeds the cellular composition from chamber 210. Input manifold carriage 221l is attached to carriage posts 221o, which are translatably received through openings in post feed mounts 221p. An electric motor, solenoid, or other powered mechanism (not shown) is mechanically coupled to posts 221o and operable to withdraw posts 221 through mounts 221p, preferably at a constant rate or in another predetermined manner, thereby causing a pull-back motion of the manifold carriage 221l and its associated cannulae 221k. The substrate 20,50 is held stably in its starting position during this pull-back operation by clamping members 224a engaging at least portions of the periphery of the substrate 20,50, or any other suitable mechanism for maintaining a registration position of the substrate relative to application device 221

(see additional discussions below pertaining to registration devices 224). With cannulae 221k initially received within passages 22 of substrate 20 or 50 with their distal tips located distally therein, an automated pull-back motion can be initiated during which the cellular composition is pumped and expressed from the tips of cannulae 221k at a predetermined rate. In this fashion, by controlling the rate of pull-back, and the rate of flow from cannulae 221k, system 200 can highly effectively seed the cell growth substrate with a given flowable cellular composition.

With continued reference now to FIG. 9, as discussed above, system 200 can include a registration device 224 for retaining the cell growth substrate 223 in a predetermined position relative to a starting or in-process position of application device 221, or otherwise within chamber 222. In this fashion, device 221 can be reliably operated to deposit the cellular composition to the substrate 223 in a desired manner. Registration device 224 can for example include upstanding walls, clamps, pins, or other features that associate with the material or shape of substrate 223 to hold the same in position within the chamber 222. Further, substrate 223 can be equipped with mechanical elements that cooperate with registration device 224 during loading into chamber 222. For example, substrate 223 could have temporarily (non-implantable) or permanently attached (implantable) strips or bars of relatively rigid plastic for reliably cooperating with a rigid structure of registration device 224 to stably position substrate 223 within chamber 222. After seeding and before implantation, such mechanical elements can be removed from substrate 223 if they are not intended or suitable for implant.

System 200 can also have a distribution assist device 225 for facilitating the distribution of the cells across or through the substrate 223. Distribution assist device 225 can therefore be operable to impart a force to the cellular composition within chamber 222 and/or resident upon substrate 223. The distribution assist device 225 may for example be operable to create a vacuum to pull the cellular composition and thus cells through the thickness of the substrate 223, to more evenly distribute the cells within substrate 223. Alternatively, distribution assist device 225 can be a magnet, such as a permanent or electromagnet, and can impart a magnetic field encompassing substrate 223. This, in conjunction with magnetic materials associated with the cells, for example, magnetite liposomes to which the cells are attached, can be used to drive the cells through and/or along the substrate 223 to distribute the cells. Alternatively, distribution assist device 225 can be operable to impart motion to the substrate 223 such as vibration or rotation, to assist in distributing the cell composition through the substrate 223. In one embodiment, distribution assist device 225 can impart rapid rotation so as to drive the cellular composition by centripetal force, and the substrate 223 can be arranged in the path of the driven cellular composition (e.g. along a substantially vertical or otherwise upstanding wall when the rotation is in the horizontal plane). Using this arrangement the cellular composition can be driven against and into the substrate 223. Still other devices 225 that impart forces to the cellular composition and/or to the substrate 223 to enhance the combination of the two can be used, including for example devices 225 that can impart pulsatile and/or bidirectional flow to liquids within chamber 222. In certain embodiments, a sheet form substrate 223 can be mounted within chamber 222 so as to divide the chamber 222 into first and second volumes, the first and second volumes fluidly sealed from one another except across the substrate. Directional flow can then be caused within chamber 222 by creating a pressure differential with the aid of distribution device 225 so as to provide transmural flow of the cell suspension across the substrate 223 to distribute cells onto and potentially also into the substrate 223. All functions of chamber 222 may be under the control of process controller 229 as discussed in greater detail hereinbelow.

In other embodiments, an extracellular matrix hydrolysate or gel material, including for example those described herein, can be charged into chamber 222 along with the cells, and a solid, three-dimensionally stable cell growth substrate can be incubated in a volume of the hydrolysate/gel and cell mixture, including while completely immersed therein. Agitation of the combined materials can be conducted as described herein. The solid, three-dimensionally stable substrate can be an ECM material as described herein, preferably retaining at least one native (endogenous) bioactive component or a combination thereof as described herein, and/or can be in the form of a sheet, filament or thread, or particulate. The combined materials can be incubated as described herein and thereafter administered to the patient.

In still further embodiments, an application device 221 can have one or more cannula(e) as described herein, and the outlet opening(s) of the cannula(e) can be positioned internally within the volume of a solid cell growth substrate 223, such as a sponge, foam or other similar fibrous substrate. The cellular fluid can then be injected into the inner volume of the substrate material 223 and can migrate under pressure toward (and potentially out of) the exterior surfaces of the substrate 223, depositing cells within the substrate on the way. In certain embodiments, the cannula(e) and its/their openings and substrate 223 can be configured to cause a substantially even flow of the fluid material through the substrate 223 in all directions from a generally central location within the substrate, so as to facilitate an even distribution of cells within the substrate 223.

During and/or after seeding of a substrate 223 and incubation for a time as described herein, system 200 can assess the seeded substrate 223 to determine whether substantial numbers of non-adhered cells remain on or in substrate 223. This can be achieved, for example, by flushing all or a portion of substrate 223 with a probing pulse of liquid to dislodge non-adhered or poorly-adhered cells, and the liquid pulse then collected and assessed for the presence of cells, including in some embodiments quantitatively. The probing pulse can for example be fed to chamber 222 via line 227 from a chamber in media unit 226 (discussed further below), or another independent source and feed line could be provided. The test pulse liquid can for example be physiological saline, preconditioning media, cell culture media, or any other liquid allowing for the displacement and subsequent detection of non-adhered or poorly-adhered cells on the substrate 223. In one embodiment, the collected pulse volume with the dislodged cells can be directed to detector 213 as discussed herein, e.g. a cell counting device utilizing the Coulter principle or another means for counting cells. If an overly high number of cells are dislodged by the probing pulse, the substrate 223 and cells can be incubated for a further period of time to allow for cell attachment. If no cells or a sufficiently low number of cells are collected in the test pulse, then the seeded substrate 223 can be removed from chamber 222 and administered to the patient. System 200 can optionally generate a signal, such as a visual and/or audible signal, to indicate that the seeded substrate 223 within chamber 222 is ready for administration to the patient. All of these operations can be under the direction of a process controller 229 discussed further below.

System 200 can also include a preconditioning media unit 226 having one or multiple chambers fluidly coupled to application device 221 via conduit 227, and powered by pump 228. Application device 221 can share duties in applying the cellular composition and preconditioning media to the substrate 223, or separate application devices can be incorporated. Preconditioning unit 226 can contain and supply media for pretreating the substrate 223 to condition the same for receipt of the cellular composition. The preconditioning media within chamber 226 can, for example, be a cell culture medium, or can contain proteins or other substances beneficial to the cells or which render the substrate 223 more compatible with survival of the cells. In one embodiment, the preconditioning media in unit 226 includes serum, preferably autologous serum from the patient to receive the cellular graft produced using system 200. The preconditioning media can be applied to the substrate 223 using the application device 221. Optionally also, preconditioning unit 226 or other components of system 200 can incorporate materials for rinsing the substrate 223 after treatment with other preconditioning media, for testing the substrate, or other operations. For these purposes chamber 222 can include a drain connected to a waste line in certain embodiments.

System 200 is preferably automated and thus includes a process controller 229 which is operable to control the various mechanisms in system 200 such as pumps, valves, temperature control units, detectors such as devices 204 and 213, the application device 221, the distribution assist device 225 and other components of system 200, to achieve the functions herein recited. Process controller 229 may be a processor-based system for controlling, either completely automatically or by assisting user control, all of the various mechanisms of system 200. Although not illustrated in FIG. 9 for the sake of clarity, process controller 229 is coupled to the various mechanisms of system 200 that it controls or from which it receives sensed data by means of appropriate input and/or output communication paths, as will be evident to those skilled in the art.

Process controller 229 may include electronic user input device(s) 230, such as a keyboard and/or a mouse, connected via connection 231. A display 232, connected via connection 233, may be provided to display status entries, results of analyses, prompts to the user, and other information as desired. A printer device 242, connected via connection 243, may be provided to produce a printed record of results of analyses, current status of the cell seeding operation, and/or a record of the operations completed by the system 200 during a cell seeding operation, and other information as desired. These devices are coupled to allow the input of user control instructions into the process controller 229 so that the system 200 may be operated as needed for the current cell seeding operation, and various forms of information may be displayed, printed or manipulated by users.

The process controller 229 may be implemented on a personal computer, a workstation computer, a laptop computer, a palmtop computer, a tablet computer, a wireless terminal having computing capabilities (such as a cell phone or personal digital assistant (PDA) having a Windows CE, a Palm operating system, or the like), or with a microcontroller integrated into the system 200. It will be apparent to those of ordinary skill in the art that other computer system architectures may also be employed, and that the particular architecture chosen is not critical to the presently disclosed systems and methods.

In general, such a process controller 229, when implemented using a computer, comprises a bus for communicating information, a processor coupled with the bus for processing information, a main memory coupled to the bus for storing information and instructions for the processor, a read-only memory coupled to the bus for storing static information and instructions for the processor. The display 232 is coupled to the bus for displaying information for a user of system 200 and the input device(s) 230 is coupled to the bus for communicating information and user command selections to the processor. A mass storage interface for communicating with a data storage device containing digital information may also be included in process controller 229, as well as a network interface for communicating with a network.

The processor may be any of a wide variety of general purpose processors or microprocessors such as the PENTIUM, CORE and XEON microprocessors manufactured by Intel Corporation, a POWER PC or POWER ISA manufactured by IBM Corporation, a SPARC processor manufactured by Sun Corporation, or the like. It will be apparent to those of ordinary skill in the art, however, that other varieties of processors may also be used in any particular computer system. Display 232 may be a liquid crystal device (LCD), a cathode ray tube (CRT), a plasma monitor, a light emitting diode (LED) device, or other suitable display device. The mass storage interface may allow the processor access to the digital information on the data storage devices via the bus. The mass storage interface may be a universal serial bus (USB) interface, an integrated drive electronics (IDE) interface, a serial advanced technology attachment (SATA) interface or the like, coupled to the bus for transferring information and instructions. The data storage device may be a conventional hard disk drive, a floppy disk drive, a flash device (such as a jump drive or SD card), an optical drive such as a compact disc (CD) drive, digital versatile disc (DVD) drive, HD DVD drive, BLUE-RAY DVD drive, or another magnetic, solid state, or optical data storage device, along with the associated medium (a floppy disk, a CD-ROM, a DVD, etc.)

In general, the processor retrieves processing instructions and data from the data storage device using the mass storage interface and downloads this information into random access memory for execution. The processor then executes an instruction stream from random access memory or read-only memory. Command selections and information that is input at input device(s) 230 are used to direct the flow of instructions executed by the processor. The results of this processing execution may then be used to control the various mechanisms in system 200.

The process controller 229 is configured to generate an output for display on the display 232 and/or for driving the printer 242 to print a hardcopy. Preferably, the display 232 is also a graphical user interface, allowing the user to interact with the displayed information.

The process controller 229 may also be configured to communicate with one or more external systems (not shown) via a network, such as a local area network (LAN), a wide area network (WAN) or the internet. Both the process controller 229 and the external systems may be configured to act as a web server, a client or both and may be browser enabled. Thus, the system 200 may access and/or store information remotely, may be controlled and/or monitored remotely, and data exchange between process controller 229 and other systems may occur.

To minimize loss of cells during transfer operations, it may be desirable to utilize as few chambers as possible in the processing of the cell suspension. Thus, in certain embodiments, system 200 can omit optimized cell formulation chamber 210 and its associated detector 213, and instead process the cell suspension to a desired condition for application to the substrate within first chamber 203. Thus, shown in phantom is conduit 234 in this alternate embodiment, fluidly connecting the chamber 203 to the application device 221. Conduit 234 can transfer an optimized cell suspension to device 221 under the power of pump 235. In this more simplified version, system 200 can also include conduit 236 feeding from formulation via chamber 216 to cell suspension chamber 203, and powered by pump 218. Accordingly, the cell suspension composition can be processed with processing media from chamber 207, and with formulation media from chamber 216, all within a single chamber 203. For subsequent processing steps with various media, chamber 203 can be equipped with means for removing applied media, such as filters as discussed above, or other devices that can remove liquid or otherwise concentrate the cells after the application of volumes of treatment media from chambers 207 and/or 216. After processing and adjustment of the cell suspension composition within chamber 203, device 204 can be used to confirm that the cell suspension composition has a cell concentration within a desired range, whereafter the composition can be advanced to application device 221 for application to the substrate 223. For convenience in handling and operation, system 200 can include a housing 237 housing some or all of the components discussed herein.

Figure 10:
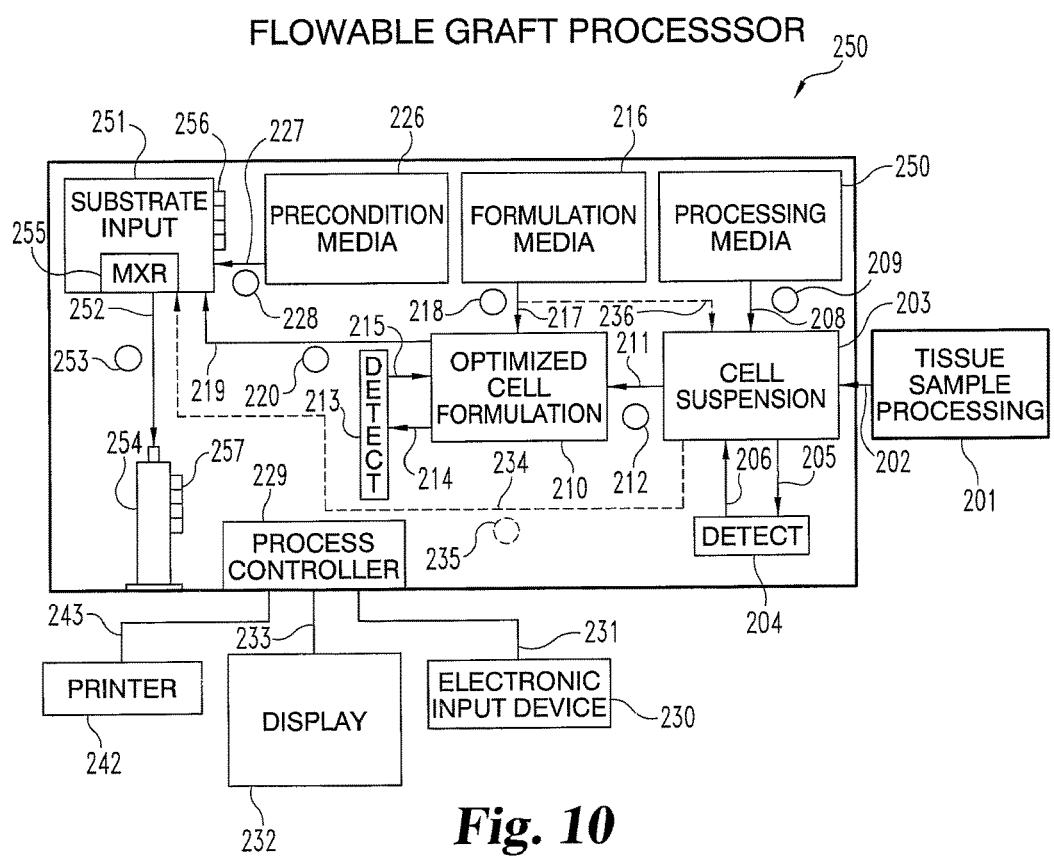
FIG. 10 provides a schematic view of another embodiment of a device for combining a cellular composition with a cell growth substrate.

Referring to FIG. 10, shown is a schematic diagram of another automated cell seeding system 250. System 250 can be used to prepare a flowable cellular graft, which in certain embodiments can be delivered by minimally-invasive techniques, such as through needles, catheters, or other percutaneously-introduced delivery devices. System 250 includes many components in common with system 200 (FIG. 9) described above, which are identically numbered in FIG. 10 and need not be described again here. As to other components, system 250 includes a cell growth substrate input chamber 251 for receiving a particulate-form substrate, a gel-form substrate or precursor materials thereto, or a combination of these, potentially also along with other materials for the graft. The processed cell suspension composition is combined with the cell growth substrate in chamber 251 via conduit 219 using optional valves (not shown) and under the power of pump 220. A prepared composition from chamber 251, including the cells and the substrate material(s), is transferred by flow via conduit 252 to a receptacle 254, using optional valves (not shown) and powered by pump 253. Such valves and/or pumps 220 and 253 may be under the control of process controller 229. Receptacle 254 can be a chamber device temporarily attached and fluidly connected to conduit 252, which can be removed to transport the cellular graft material away from system 250. Receptacle 254 can thus be a vial, bag, or other container fluidly connected to conduit 252. In certain embodiments, receptacle 254 can comprise a delivery device for delivering the cellular graft composition to the patient, or a component thereof. In one embodiment, receptacle 254 includes a chamber, illustratively a syringe barrel, from which the cellular graft composition will be forcefully expelled for delivery to patient tissue by a fluidly coupled needle, catheter, or other minimally-invasive device. System 250 can include structural mating features for insertion and mating of such a receptacle 254 in a fashion that fluidly couples to conduit 252 for receipt of a prepared, flowable cellular graft material.

Chamber 251 can be equipped with a device 255 that mixes materials within chamber 251. Device 255 can be comprised of a mechanism located completely external of chamber 251, but which imparts motion to chamber 251 or parts thereof to mix components therein. For example, such a device can comprise a vibrator, a shaker, a rotary element such as a vortexer, or a static mixer positioned in a flow path for the components to be mixed. Device 255 can also be comprised of a mechanism located within chamber 251 such as a paddle, a stir bar, or impeller, such mechanism driven by a motor or other means, so as to agitate flowable compositions received within chamber 251. Device 255 can also be comprised of components both internal and external of chamber 251, such as an external moving (e.g. rotating) magnet that drives a magnetically-coupled paddle, stir bar, or other element within chamber 251. Device 255 may be under the control of process controller 229.

In addition to providing mixing within chamber 251, system 250 can include a thermal control device 256 associated with chamber 251 and/or a thermal control device 257 associated with receptacle 254, operable to control the temperature of respective materials therein. Thermal control devices 256, 257 may be under the control of process controller 229, and may contain appropriate temperature sensing elements to provide current temperature feedback readings to facilitate the regulation of temperature. Thermal control device 256 can be a heating element and/or cooling element. In certain modes, thermal control device 256 can be operated to control the temperature of a material within chamber 251 and thereby regulate its viscosity. Illustratively, the cell growth substrate composition received within chamber 251 may comprise a gellable material, and thermal control device 256 can be operated to maintain the material in an ungelled state prior to and during its combination with the cell suspension fed from conduit 219. In this manner, the less viscous state of the substrate material will allow a more facile mixing with the cell suspension material. In this use, for gellable materials that increase in viscosity with decreasing temperature, thermal control device 256 will be operated so as to heat the materials within chamber 251. In this regard, the heating will desirably be conducted to avoid any significant thermal damage to the cells, for example heating to a temperature of less than about 42° C. when cells are present. In certain embodiments, the gellable material within the substrate composition will be selected so that it gels at a temperature of 37° C. or slightly above. For mixing with the cell suspension to achieve a substantially homogenous composition, the material can be heated at a temperature above its gel point, but below a temperature at which the cells would be significantly damaged (e.g. below about 42° C.). After mixing, the cell/substrate composition can be maintained above the gel temperature of the substrate material prior to and during delivery to a patient, for example using thermal control device 257. In this fashion, a less viscous (and more flowable) delivery state is provided during delivery, e.g. through a needle or other cannula, but the material will gel and thus increase in viscosity after delivery to the patient (e.g. a human patient having a normal body temperature of about 37° C.) to facilitate maintenance of the delivered graft material at the site of administration. Alternatively, after mixing to provide substantial homogeneity, the cell/substrate material can be allowed or caused to gel external of the patient (e.g. by cooling with device 256 and/or 257), and can then be delivered as a more viscous graft.

For gellable substrate materials that gel or otherwise increase in viscosity with increasing temperature, thermal control device 256 can be operated so as to cool the materials within chamber 251. In this regard, the cooling will desirably be conducted to avoid any significant freeze damage to the cells, for example cooling to a temperature of greater than about 0° C. In certain embodiments, the gellable material within the substrate composition will be selected so that it is gelled or otherwise increases in viscosity at a temperature of about 37° C., as compared to lower temperatures, for example about room temperature (about 25° C.) or below. For mixing with the cell suspension to achieve a substantially homogenous composition, the material can be cooled with device 256 to retain a less viscous condition. After mixing, the cell/substrate composition can be maintained in a cooled state using thermal control device 256 and/or 257 prior to and during delivery. In this fashion, a more flowable state is provided during delivery, e.g. through a needle or other cannula, but the material will increase in viscosity after delivery to the patient (e.g. a human patient having a normal body temperature of about 37° C.) to facilitate maintenance of the delivered graft material at the site of administration. Alternatively, after mixing to provide substantial homogeneity, the cell/substrate material can be warmed, e.g. using device 256 and/or 257, or allowed to warm in an ambient setting, for delivery as a more viscous graft.

Conditions other than temperature can also be used to cause cell growth substrate materials to gel when desired (e.g. after a mixing operation with cells). For example, collagenous materials can be selected that gel with increasing pH. During a mixing operation within chamber 251, the pH of the substrate/cell composition can be maintained at a relatively lower level at which the composition remains more flowable, but at which the cells can survive, at least during the period of mixing. Illustratively, such a pH may be in the range of about 4 to about 6.5. After mixing, the pH of the composition can be increased so as to cause the collagenous material to gel and increase the viscosity of the graft material. Such a pH adjustment may be accomplished by adding a biologically compatible base or buffer, or both. These additives may be provided from a chamber in unit 226, or another reagent chamber in provided in system 250. The post-mixing pH of the composition can, for example, be in the range of above about 6.5 up to about 8. Desirably, the post-mixing pH will be one which is suitable for administration to a patient, which in certain specific embodiments will be about 7 to about 7.5.

After combination of a cell growth substrate material with a cellular composition in system 200 or 250 discussed above, the seeded graft material can be immediately administered to a patient. In other embodiments, the cell seeded graft material can be incubated ex vivo for at least a period of time sufficient to achieve attachment of at least some of the cells to the cell growth substrate, and desirably a substantial percentage of cells, for example greater than about 20% of the originally-provided cells. Such cell-attachment incubation phases can have a duration of one minute up to about five hours, and in particular embodiments about five minutes up to about three hours. During this period, the composition will be maintained under conditions in which cells in the composition, at least in part through their native capacity to attach to surfaces, attach to cell growth substrate sheets, particles or other material(s) in the combined composition. Cell attachment phases or cycles can be conducted during which no significant expansion of the number of originally-provided cells is experienced, for example wherein the composition has no more than ten percent greater viable cells than those originally combined with the cell growth substrate, and in certain embodiments wherein the composition as essentially the same number of cells or fewer cells than the number originally combined with the cell growth substrate.

In the preparation of flowable graft materials in automated system 250, the composition can optionally be continuously or periodically agitated during a cell attachment phase as discussed above, for example using mixer device 255. In particular embodiments, mixer device 255 will be used to periodically gently agitate the composition during a cell attachment cycle, with relatively static cell attachment phases occurring between agitation phases. For example, multiple non-agitated phases may have a duration of about three minutes to about twenty minutes each, interrupted by shorter agitation phases, for example of about ten seconds to five minutes, performed gently so as to bring additional suspended free cells into contact with cell growth substrate particles or material but avoid significant dislodgement of cells already attached to substrate materials.

During and/or after seeding of a substrate and incubation for a time within chamber 251 as described herein, system 250 can assess a flowable substrate cell/substrate mixture to determine whether substantial numbers of non-substrate-adhered cells remain in the suspending medium of the mixture. This can be achieved for example by filtering the sample upon collection to remove the substrate material with adhered cells, leaving only cells freely suspended in the suspending medium. The free suspended cells can then be routed to detector 213 or another independent detector, and the cells counted utilizing the Coulter principle, light scattering or another means for counting cells as discussed herein. In another mode, the entire medium from chamber 251 can be sampled and tested (e.g. including particulate substrate, suspending medium and cells) utilizing the Coulter principle, light scattering or another means. The assessed values for the medium (e.g. scattering or electrical resistance) will vary in accordance with what percentage of the cells are adhered (e.g. to substrate particles) versus freely suspended, and thus the assessed values can be correlated to an acceptable level of cellular adherence to the substrate. If an overly high number of cells remain free in the suspending medium, the substrate and cells can be incubated for a further period of time to allow for cell attachment. If no cells or a sufficiently low number of cells remain free in the suspending medium, then the seeded substrate material can be removed from chamber 251 and administered to the patient. As with system 200, system 250 can optionally generate a signal, such as a visual (e.g. on display 232) and/or audible signal, to indicate that the seeded substrate material within chamber 251 is ready for administration to the patient. All of these operations can be under the direction of process controller 229.

In systems 200 and 250 disclosed above, the recited chambers can be provided by any suitable arrangement including for example bags, vials, passages, plastic containers, or the like. The recited conduits can be provided by appropriate tubing, lumens occurring through larger plastic structures of the system, or any other suitable arrangement. As well, it will be understood that valves can be provided within the chambers and/or the conduits, to coordinate with pumps or other material transfer means to selectively permit or prevent flow as appropriate to the circumstance. These and other physical system features will readily occur to those skilled in the art given the disclosures herein.

Systems 200 and 250 can be configured to provide a relatively short residence time for the cellular graft materials prior to implantation into a patient, for example up to about three hours. Such configurations will typically be designed to achieve attachment of the cells to a substrate, without any significant expansion of cell numbers (e.g. no expansion, or less than a 10% increase in cell numbers). However, systems 200 and 250 can in certain embodiments be configured for longer term incubation and culture of the cellular graft materials to achieve expansion of the number of cells as compared to the number originally seeded onto the substrate, for example greater than a 20% increase in the number of cells, and in some embodiments at greater than a 100% increase. For these purposes, systems 200 and 250 can also include mechanisms for imparting forces, for example shear forces, strain, or tensile forces, to the substrate during the culture period. These forces can impact the growth and differentiation of the seeded cells during the incubation/culture period, and lead to protein expression patterns that differ relative to the same cells if incubated/cultured in the absence of the forces. In this manner, the cellular grafts can be enhanced to a given end use in a patient.

As well, in certain embodiments, system 200 or 250 can include a secondary cell incubation chamber isolated from chamber 222. Cells that differ from those incubated in chamber 222 can be cultured in the secondary chamber so as to secrete signaling molecules such as hormones, cytokines, growth factors, or others, which are transferred to chamber 222. The signaling molecules can contact the cells under culture in chamber 222, for example to modulate their growth or differentiation. Transfer of the signaling molecules from the secondary incubation chamber to chamber 222 may for example be accomplished by pumping them through a conduit, by flow across a membrane, or other means. In some forms, the signaling molecules can be effective to drive a higher percentage of stem or progenitor cells cultured in chamber 222 down a given differentiation pathway. Control of the secondary cell incubation chamber may be by means of process controller 229 or by means of a separate process controller optionally in communication with process controller 229, as discussed hereinabove.

Particulate Multicellular/Substrate Graft Materials

In certain inventive embodiments, a flowable cellular graft material is provided that includes multicellular bodies suspended in a liquid medium, wherein the bodies are each comprised of a cell growth substrate particle having cells adhered thereto. The substrate particles can have a maximum cross sectional dimension of about 20 microns to about 2000 microns, and in certain embodiments about 100 to about 1000 microns. The substrate particles can be substantially uniform in size relative to one another, e.g. having maximum cross sectional dimensions within about 20%, or 10%, of one another, or can vary in size with respect to one another (e.g. having some smaller particles and some larger particles, potentially a controlled overall population created by mixing two or more substantially uniform particle populations, where the populations are of different sizes relative to one another). In advantageous variants, the substrate particles are in sheet form, and can have a sheet thickness of about 20 to about 2000, more preferably about 20 to about 500 microns, and/or a maximum cross sectional axis length considered in the plane of the sheet (e.g. height or width) that is greater than the sheet thickness and in the range of about 25 to about 2500 microns, more preferably about 100 to about 1000 microns. The sheet thickness can be in the range of about 20 to 1000 microns, and/or the maximum cross sectional axis length considered in the plane of the sheet can be in the range of about 100 to about 1500 microns, in certain embodiments. In addition or alternatively, the substrate particles can be relatively rounded or compact, as opposed to long and fibrous, when considered in the plane of the sheet. The substrate particles can have shapes that are regular with respect to one another or which are irregular with respect to one another. In certain embodiment, the particles can be sheet form particles having a generally circular, ovoid and/or polygonal (e.g. having three to ten sides, e.g. triangular, square or otherwise rectangular, pentagonal, hexagonal, etc.) shape. For example, the substrate particles, or a substantial percentage of them in the composition (e.g. above about 25%), when considered in the plane of the sheet, can have a maximum cross sectional dimension axis which is no more than about two times the length of the cross sectional dimension axis taken on a line perpendicular to and centered on the maximum cross sectional dimension axis; preferably, at least about 50% of the substrate particles will have this feature, and more preferably at least about 70% of the substrate particles will have this feature. Such particulate cell growth substrate materials also constitute an embodiment of the present invention, alone (e.g. as cell-free tissue graft materials) or used in combination with cellular compositions as discussed herein.

Small, sheet-form substrate particles as discussed above can be cut from larger sheets of substrate material. In certain embodiments, the larger sheet of substrate material will be an extracellular matrix sheet material harvested from a tissue source and decellularized, as discussed herein. Sheet-form particles having the above-described characteristics can be cut from larger ECM sheets using mechanical implements such as punches or dies, or by cutting using lasers, or using any other suitable means. In desired embodiments, the cutting method used will not eliminate the native bioactive ECM character or native bioactive ECM molecules, as discussed in more detail herein, when this character or these molecules are resident in a larger starting ECM sheet being processed. Additionally, the ECM sheet being processed, and the resultant ECM sheet particles can have a retained native epithelial basement membrane on one or both sides of the sheet material, and/or biosynthetically deposited basement membrane components on one or both sides of the sheet. To provide native epithelial basement membrane on both sides of the sheet, two isolated decellularized ECM layers, each having a single basement membrane side and an opposite side, can be stacked and fused or bonded to one another with the basement membrane sides facing outwardly. The resulting bilayer sheet can then be processed to form the sheet-form particles as described above. To prepare particles with deposited non-native basement membrane components, a decellularized ECM sheet can be conditioned by growing epithelial, endothelial or other cells on both sides to deposit basement membrane components. The cells can then be removed while leaving the basement membrane components, and the sheet then processed to prepare the sheet-form particles as described above.

Figure 11:
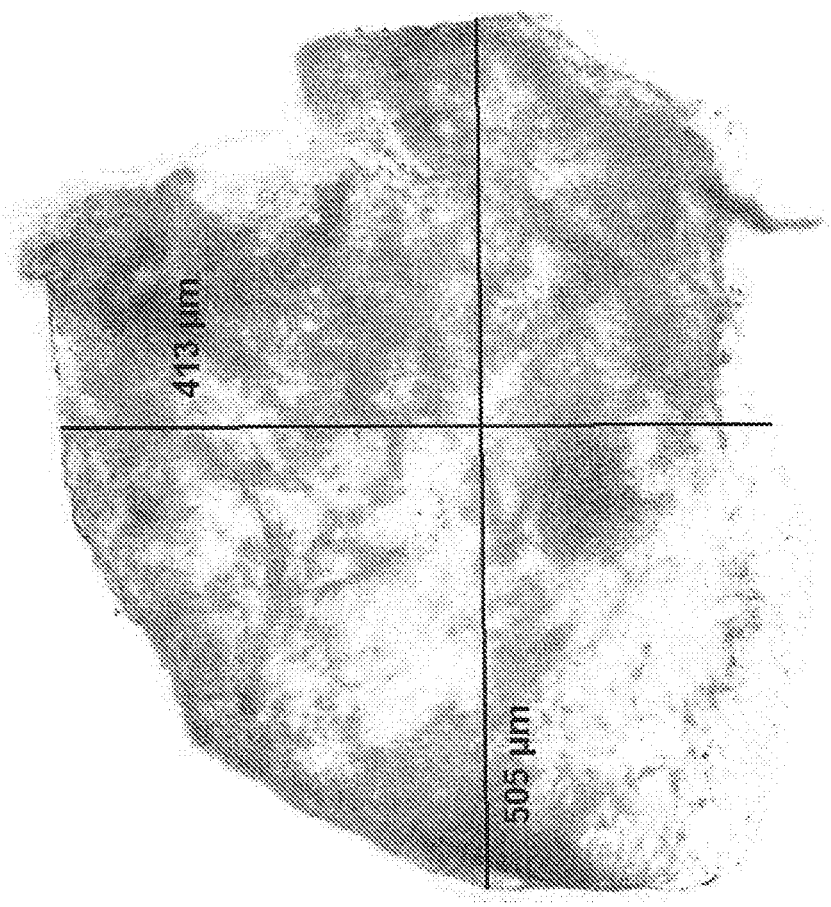
FIG. 11 is a digital image of a compact sheet particle of a decellularized ECM sheet, compositions of which are useful as cell growth substrates.
Figure 11A:
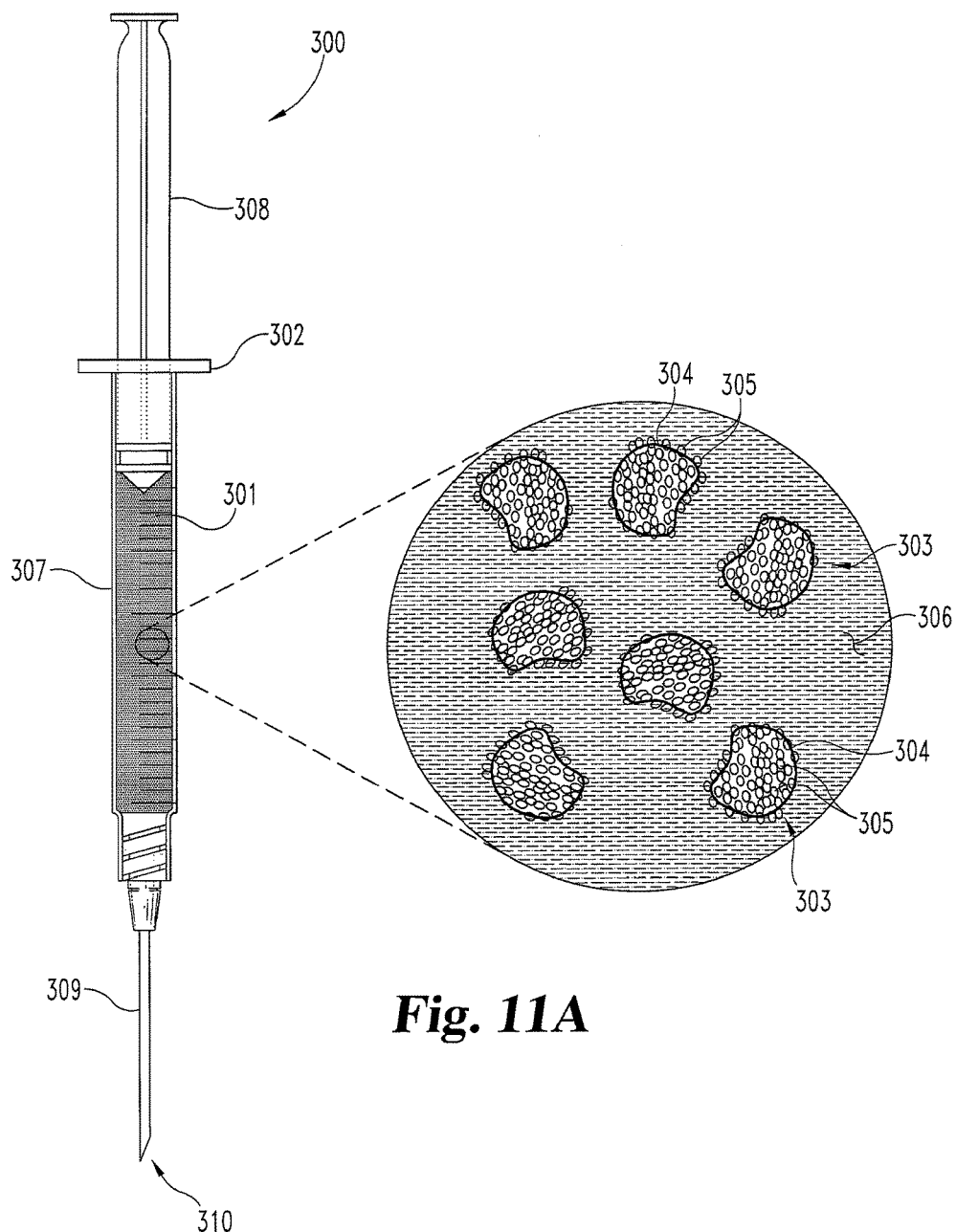
FIG. 11A provides an illustration of a flowable cell graft material of the invention, combined with a delivery device.

FIG. 11 provides a digital image of an illustrative, very small ECM "dot" that was laser cut from a larger ECM sheet. In this particular illustration, the ECM sheet utilized was single layer porcine small intestinal submucosa, as available from Cook Biotech Incorporated, West Lafayette, Ind., USA. As can be seen, the length of the maximum cross sectional axis in the plane of the sheet is about 505 microns, whereas the length of the cross sectional axis on a line perpendicular to and centered on the maximum cross sectional axis is about 413 microns. Accordingly, these two length dimensions are within about 25% of one another, providing a compact sheet particle structure. ECM particulate compositions having greater than about 50% of the particles exhibiting this level of correspondence in length dimensions can be especially beneficial in use, particularly where greater than about 50% of the particles have a maximum cross sectional axis in the plane of the sheet in the range of about 100 to about 1000 microns.

To prepare a cell seeded graft composition, particulate growth substrate as described above can be combined with a cellular preparation, for example using system 250 described hereinabove. For flowable grafts, the particulate growth substrate can be suspended in a liquid medium, such as an aqueous medium. Prior to administration, the graft composition can be incubated during a cell attachment cycle, such as any of those discussed above. The size and relatively planar compact shape of the particulate cell growth substrate provides advantageous suspension and cell attachment characteristics, which can also be enhanced when a flexible substrate material, such as an extracellular matrix sheet material, is used. For administration to the patient, the flowable cell seeded graft can be loaded in a syringe or other delivery device, and the graft delivered to a tissue targeted for grafting. Illustratively, with reference to FIG. 11, shown is a medical device 300 including a flowable cellular graft composition 301 loaded in a syringe 302. Cellular graft composition 301 includes a plurality of cellularized bodies 303 that include a matrix particle 304, as discussed here and above, and a population of cells 305 attached to each matrix particle 304. In certain embodiments the cells 305 form a generally confluent layer of cells covering the matrix particle 304. The cellularized bodies 303 are suspended in a liquid medium 306, such as an aqueous medium optionally containing nutrients for the cells, and which is physiologically compatible with a human or other patient. Cellular graft composition 301 is flowable and received within the barrel 307 of the syringe 302. A plunger 308 is received within barrel 307 and operable upon linear actuation to drive composition 301 through the fluidly coupled needle 309 and out the opening 310 thereof. Medical device 300 can therefore be used to administer the composition 301 into tissues of the patient. In certain preferred embodiments, the target tissues are in need of revascularization and the cellular graft bodies 303 include cells 305 capable of forming blood vessels, for example endothelial cells or endothelial progenitor cells, including in certain embodiments endothelial colony forming cells as discussed herein. Upon injection into the target tissue, the matrix particles 304 will assist in retention of the cells 305 in the targeted region. In particularly preferred embodiments, particles 304 are extracellular matrix particles as described herein.

Cellular Grafts with Gel-Coated Matrix Substrates

Cellular grafts of the invention can have a porous matrix cell growth substrate that is at least in part coated with a gel, such as an extracellular matrix gel, with the cells incorporated within the gel, on the surface of the gel, or both. The gel can be applied to the porous matrix substrate before, after, or in admixture with the cells, or any combination of these. The gel can incorporate substances that enhance the ability of cells to attach to the substrate, such as fibronectin, laminin, collagen I, or other material(s). When applied in admixture with cells, the gel, or precursor material(s) to the gel, can be applied in a less viscous (e.g. ungelled state) to facilitate application to the substrate and if desired penetration into the porous network of the substrate along with the cells. The gel or gellable precursor(s) can then be allowed or caused to gel or otherwise increase in viscosity to promote rapid adherence of the gel and cells entrained therein to the porous matrix substrate. In certain embodiments, the gel is comprised of an extracellular matrix gel, for example as described in United States Patent Application Publication No. US20070082060 published Apr. 12, 2007, publishing U.S. patent application Ser. No. 10/569,218 filed Aug. 25, 2004, which is hereby incorporated herein by reference in its entirety. Accordingly the gel can include an ECM hydrolysate composition prepared by digesting ECM tissue such as that described herein with acid and/or enzyme, which composition is gellable upon increasing the pH to about 6.8 to about 8, and/or upon increasing the temperature of the material to about 37° C. Such compositions can contain native collagen and native (endogenous) bioactive non-collagen components of the starting ECM material such as growth factors, glycosaminoglycans, proteoglycans and/or other materials as discussed in conjunction with ECM materials below.

System 200, discussed above, can be used to prepare these cellular grafts with gel-coated matrix substrates. For example, a gel or gel precursor(s) can be applied to the substrate 223 using application device 221. For application of the gel material prior to the cells, the gel or gel precursor can be fed from precondition media unit 226 and applied to the substrate 223. For combination of the cells with the gel or gel precursor(s) prior to application to the substrate, the cellular and gel materials can be mixed in-line by combining the feeds from conduits 219 and 227 prior to release from application device 221, or the cellular material can be combined with the gel or gel precursor(s) within a chamber of precondition media unit 226, or another chamber, prior to feed to the application device 221. Temperature and/or pH control can also be provided by system 220, if needed, to facilitate an increase in viscosity of the applied material after it is in contact with substrate 223. Illustratively, for pH adjustment, an amount of a basic substance, such as NaOH, can be combined with the cell/gel precursor composition immediately prior to application to the substrate 223, whereupon the complete gelling of the material will be sufficiently delayed for application to the substrate 223 and subsequent firming. Alternatively, the substrate 223 can be preconditioned with a basic or buffer substance to neutralize and increase the pH of a more acidic cell/gel precursor material upon contact with the substrate 223. Still further, the temperature of the cell/gel precursor material can be increased by a heating element before and/or after application to the substrate 223. These and other gel-forming adjustments to conditions can be automated by system 200.

Cellular Graft Filaments

Figure 12:
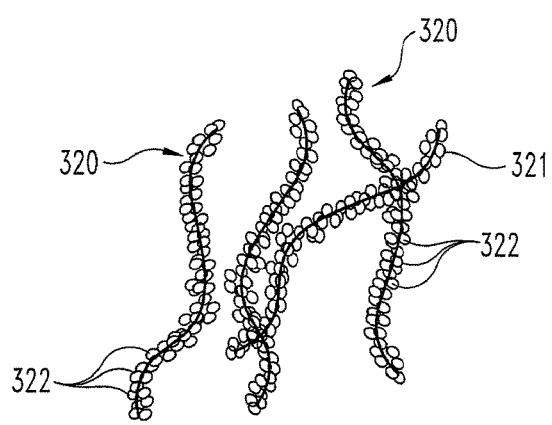
FIG. 12 provides an illustration of cellularized filament grafts of the invention.

In additional embodiments, the invention provides cellular grafts which include a cell growth substrate in the form of an elongate filament, with a population of cells attached along the filament. In these embodiments, the filament can have a length of at least about 1 mm, for example in certain embodiments in the range of about 1 to about 30 mm, or about 5 to about 30 mm. The filament can also have a greatest cross sectional dimension of about 20 microns to about 2 mm, or about 100 microns to about 1 mm. Extracellular matrix substrates as described herein are preferred for these purposes. To prepare such cellular grafts, the elongate substrate can be incubated in the presence of a cell suspension containing the desired cells for at least a period of time sufficient for cell attachment to the substrate, for example in an automated system such as system 200 or system 250 described herein. Referring to FIG. 12, shown is a diagrammatic illustration showing several cellularized filament grafts. Each cellularized filament graft 320 includes the elongate cell growth substrate 321 and a population of cells 322 attached to the substrate 321. The cells 322 can in certain embodiments form a generally confluent layer covering the cell growth substrate 321. To accomplish this, sufficient originally-provided cells can be attached to the substrate 321 to form the layer, or the substrate filaments 320 can be seeded and then cultured sufficiently to form the generally confluent layer. In use, the cellularized filament grafts 320 can be introduced individually into a site for treatment, for example by positioning each strand cellularized filament graft 320 longitudinally within the lumen of a needle, inserting the needle into a desired target tissue, and driving the graft 320 from the needle with fluid pressure. The graft 320 will thereby distribute cells 322 through an elongate region of the target tissue. This may be useful, for example, where the development of a vascular vessel or vessels in that region is desired. For these purposes, vessel-forming cells, such as endothelial cells or endothelial progenitor cells, including ECFC cells as discussed herein, can be used. In alternative embodiments, a flowable cell graft suspension containing a plurality of elongate filament grafts 320 can be provided within a syringe and injected into a target tissue. Such a suspension and a medical product for delivery thereof can be similar to product 300 depicted in FIG. 11, except using elongate grafts 320 instead of, or in addition to, the relatively more compact particulate cellular graft bodies 303.

Figure 12A:
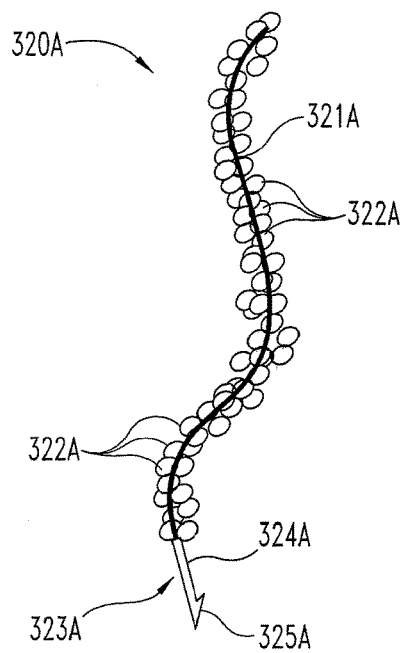
FIG. 12A provides an illustration of a cellularized filament graft of the invention having a distal retention barb.

Referring now to FIG. 12A, shown is another cellularized filament graft 320A of the invention. Graft 320A can have features which are the same as graft 320 discussed above, including an elongate filament substrate 321A and a population of cells 322A attached to the substrate. Graft 320A further includes a patient tissue-engaging anchor element, which in the illustrated embodiment is shown as a barb or hook 323A having a stem 324A and a tissue engaging barb end 325A. The barb 323A or other anchoring element in the illustrated embodiment is attached at or approximate to an end of the filament substrate 321A. This attachment can be by tying, welding, bonding, integral formation with, or any other suitable means. The anchoring element such as barb 323A in certain embodiments resists passage through tissue in one direction greater than in an opposite direction. This can be achieved for example by the directional barb 325A. The barb 323A or other anchoring element can be made of a persistent material or of a bioresorbable material. Illustratively, persistent or bioresorbable materials can be made from metals or polymeric materials. Suitable bioresorbable polymers include polymers of glycolic acid, polymers of lactic acid, or copolymers of glycolic acid and lactic acid, polycaprolactone, and other known materials. In use, the barb 323A or other anchoring element will resist migration of the graft 320A once implanted in tissue of the patient, such as muscular or other tissue.

Figure 12B:
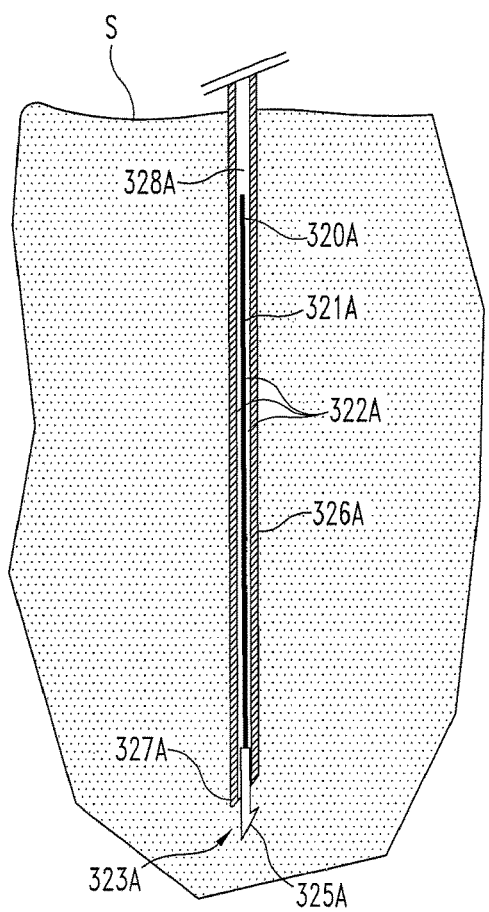
FIG. 12B provides an illustration of the graft of FIG. 12A received in a delivery needle cannula in use to implant the graft.

With reference now to FIG. 12B, in one mode of use, graft 320A can be combined with a delivery cannula 326A, such as a needle cannula. In one form, the graft 320A can have all or a portion of the filament substrate 320A received within a lumen 328A of the cannula 326A. Likewise, the barb element 323A can be partially or wholly received within cannula 326A, or, barb 323A can be resident completely out of cannula 326A, for instance carried distally thereof. In the illustrative embodiment, stem 324A or at least a portion thereof is received within the lumen in the distal region of cannula 326A, and the barb end 325A is positioned beyond the tissue-penetrated distal tip 327A of cannula 326A (e.g. needle tip). With the combined device in this condition the cannula 326A and barb 325A can be used to penetrate into tissue of the patient targeted for receipt of the graft 320A, by penetrating the patients skin "S" and driving the same to the desired depth in the underlying tissues. Thereafter, upon applying a withdrawing force to cannula 326A, the barb tip 325A will engage tissue of the patent and resist withdrawal while the cannula 326A is withdrawn thereby delivering the graft 320A from the lumen 328A as the cannula 326A is withdrawn. Graft 320A will then be left implanted in the patent and cellular population 322A can in certain embodiments proliferate in the treatment of the patient. In some inventive variance, cellular population 322A includes endothelial cells and/or endothelial progenitor cells, including for example endothelial colony forming cells as discussed herein. The tissue to be treated and in which graft 320A is implanted can be tissue in need of vascular development, for example ischemic tissue of the myocardium or ischemic tissue resultant of critical limb ischemia. In such uses, cellular population 322A will be implanted positioned in an elongate region along substrate 321A and can generate a vessel or vessels along the elongate implant region. It will be understood, however, that other types of cellular population 322A and other diseases, defects, or conditions can be treated using filament graft 320A.

Cellular Grafts with Stacked Substrate Layers

Figure 13:
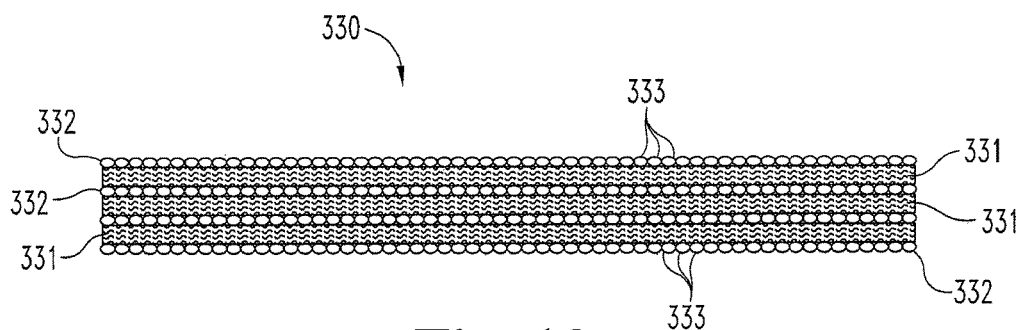
FIG. 13 provides an illustration of a cell graft of the invention having multiple, stacked cell growth substrate sheets.

Cellular grafts of the invention can also include multiple cell growth substrate sheets in a stacked configuration, with cellular populations interposed between the stacked sheets, and potentially also providing outermost layers of the construct. To prepare such grafts, a first cell growth substrate layer can be seeded with cells, for example by applying a liquid film containing a cell suspension to at least one side of the sheet. A second substrate layer can then be stacked onto the first substrate layer against the side that had received the liquid film, followed by applying another cellular liquid film to the exposed side of the second substrate layer. This process can be repeated if desired to provide a stacked substrate construct, with cells distributed evenly or regionally through the thickness of the construct. FIG. 13 provides a schematic diagram of one such stacked graft construct 330. Construct 330 includes a plurality of stacked cell growth substrate layers 331, desirably harvested, purified extracellular matrix tissue sheets as described herein. The stacked layers 331 can be partially or completely overlapped with one another. Cellular layers 332 each comprised of a population of cells 333 are provided between sheets 331, and optionally also to the outermost surfaces of construct 330. Prior to implantation, construct 330 can be incubated for a period of time at least sufficient for cellular attachment to sheets 331, which can contribute to the stability of the construct as an integral graft unit. In one alternative, the construct 330 is incubated during a culture period to expand the originally-seeded population of cells. Also, prior to applying cells 333 to the sheets 331 during fabrication of the construct 330, the sheets 331 can be preconditioned with blood components such as serum or serum protein(s) and/or with other culture media components, e.g. nutrients, salts, etc.

Stacked cellular graft constructs such as construct 330 can be prepared in automated systems such as system 200 of FIG. 9. To do so, a first substrate sheet 331 can be provided in chamber 222, and application device 221 can be used to apply a processed cell suspension to the upper surface of the sheet 331. A second substrate sheet 331 can then be overlaid onto the first sheet, and application device 221 used to apply additional amounts of the cell suspension to the second sheet 331. This process can be repeated multiple times, for example, two, three, four or five times. Additionally, preconditioning media can be supplied from media unit 226 and applied to the respective sheets 331 prior to the application of the cell suspension. The first, second, and subsequent sheets can be sequentially positioned within chamber 222 manually by a user or using an automatic feed mechanism provided by system 200.

Figure 17:
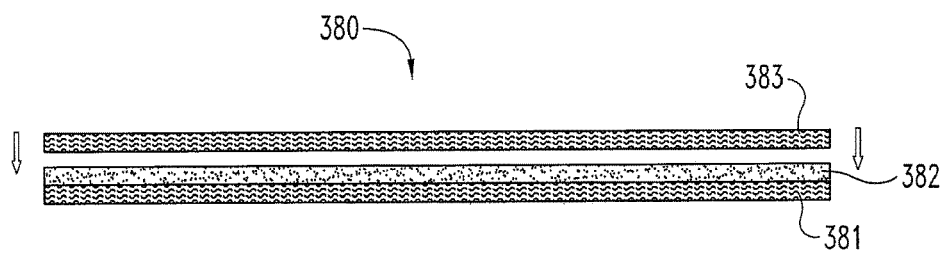
FIGS. 17 and 18 provide illustrations of additional cell graft constructs of the invention.

FIG. 17 shows another embodiment of a cellular graft of the invention having stacked growth substrate sheets. Cellular graft 380 includes a first cell growth substrate sheet 381, desirably any of the extracellular matrix layers identified herein, and a cellular material 382 deposited on a surface of sheet 381. Cellular material 382 can include any of the cells identified herein along with a flowable cell growth material or substrate for example a particulate cell growth substrate as described herein and/or a gel cell growth substrate material as described herein. After deposition of the material 382 on the surface of sheet 381, a second cell growth substrate sheet 383 is layered over material 382 to create a stacked or sandwiched cellular graft.

Figure 18:
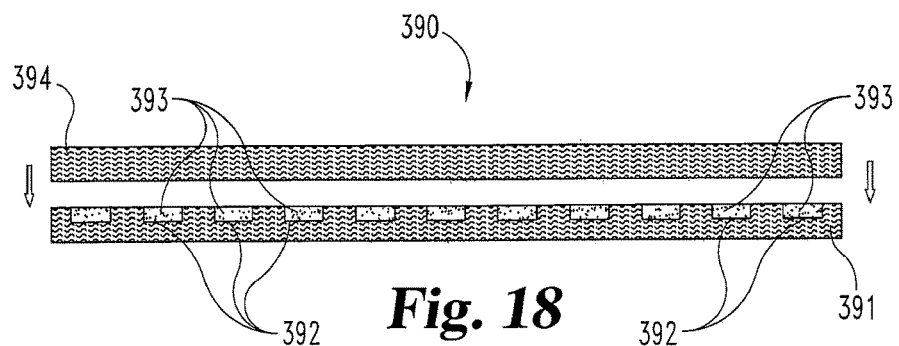

FIG. 18 illustrates still another embodiment of a cellular graft of the invention. Graft 390 includes a first cell growth substrate sheet 391 having a plurality of wells 392 defined therein and extending only partially through the thickness of sheet 391. A cellular material 393 is deposited within wells 392. Cellular material 393 can for example be simply a cell population or can be cells combined with a flowable cell growth material such as a particulate substrate or gel-formed substrate or combination thereof, as described further herein. A second cell growth substrate sheet 394 is layered over the first sheet 391 so as to cover the filled wells 392 and optionally at least temporarily entrap cellular material 391 within wells 392. Cell growth substrate sheet 391 and/or 394 and certain embodiments are any of the ECM layers as described herein.

Cell Growth Substrate Articles with Flow-Directing Layers

Figure 14:
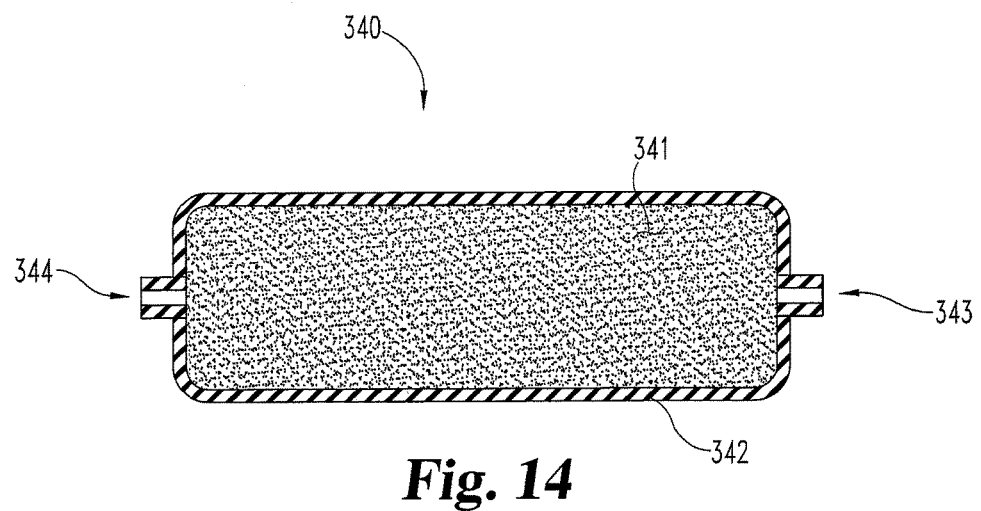
FIGS. 14 to 16 provide illustrations of cell growth substrate articles of manufacture of the invention.

The invention also provides articles of manufacture that include a cell growth substrate material covered or encapsulated within a second material that is less permeable to fluids such as aqueous cellular compositions than the cell growth substrate material, wherein the covering or encapsulating material can facilitate directing flow of a cellular fluid through a length or thickness of the cell growth substrate material to aid in distributing the cells throughout the material. Referring to FIG. 14, shown is a cell growth substrate article 340 that includes a cell growth substrate material 341 such as any described herein, and a permeable or semi-permeable encapsulating material 342 enclosing the cell substrate material 341. The encapsulating material 342 can define a first opening 343 and a second opening 344 spaced from the first opening 343. In certain embodiments, the openings 343 and 344 will occur on opposed sides of the cell growth substrate material 341. Further, a plurality of openings 343 and/or 344 could be provided in alternative embodiments. In use, article 340 can be connected to a source of a liquid cellular suspension and the suspension passed into opening 343 under pressure, to thereby drive the cellular suspension material through the cell growth substrate 341 to cause cells to adhere or become lodged within the substrate 341. The fluid of the cell suspension can exit via opening 344, depopulated of at least some of the original cells. Optionally, fluid exiting opening 344 can be recirculated back through opening 343 to seed at least some remaining cells within substrate 341. The cell growth substrate material 341 can be any monolithic, particulate, or other cell growth substrate material described herein. The encapsulating material 342 can be implantable within the patient, or can be a material not intended for implant which can be removed prior to implant of the cell growth substrate 341 after seeding with cells. Encapsulating material 342 can for example be a natural or synthetic polymeric material, which can be persistent or bioresorbable upon implantation. Bioresorbable synthetic polymers, such as those disclosed elsewhere herein, can be used for encapsulating material 342.

Figure 15:
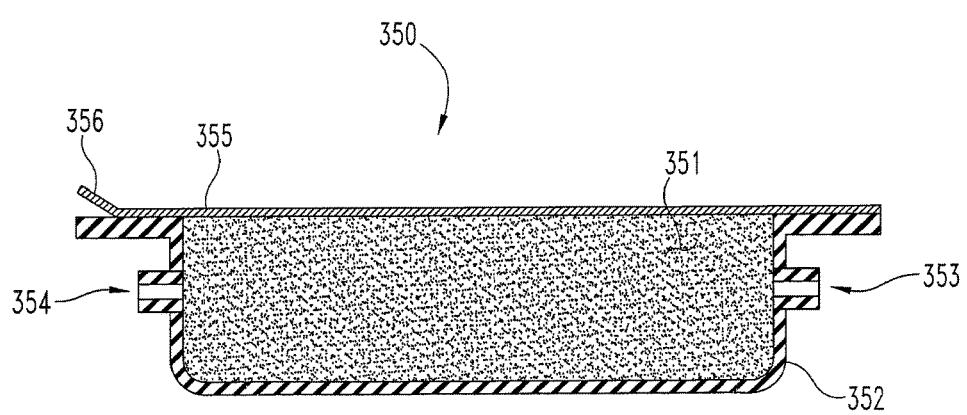

Referring to FIG. 15, shown is another cell growth substrate article of the invention. Article 350 includes a cell growth substrate 351 such as any of those disclosed herein, and a first encapsulating material 352 in which material 351 is received. Encapsulating material 352 is less permeable to a liquid in which cells are suspended or to be suspended, for example water or another aqueous medium, than the substrate material 351. Encapsulating material 352 can for example be a plastic or other polymeric tray in which material 351 is received. The tray or other encapsulating material 352 can define a first opening 353 and a second opening 354 spaced from the first opening 353. A second encapsulating material 355 covers and seals an opening defined by tray or other material 352. Encapsulating material 355 can for example be a polymeric film peelably removable from tray or other encapsulating material 352. For these purposes, film or other material 355 can include an exposed and grippable portion 356, desirably at a periphery thereof, which can be gripped and used to peel material 355 away from tray or other material 352 to open the opening defined by tray or other material 352 and expose the cell growth substrate 351 for removal. In this manner, during a cell-seeding operation such as that discussed above in conjunction with FIG. 14, material 355 will maintain a seal against material 352 and thus enclose cell growth substrate 351 to help guide fluid from opening 353 to opening 354 to seed cells through the volume of material 351. After the seeding process, the encapsulating material 355 can be peeled from the material 352 and the seeded substrate 351 removed for implant into the patient.

Figure 16:
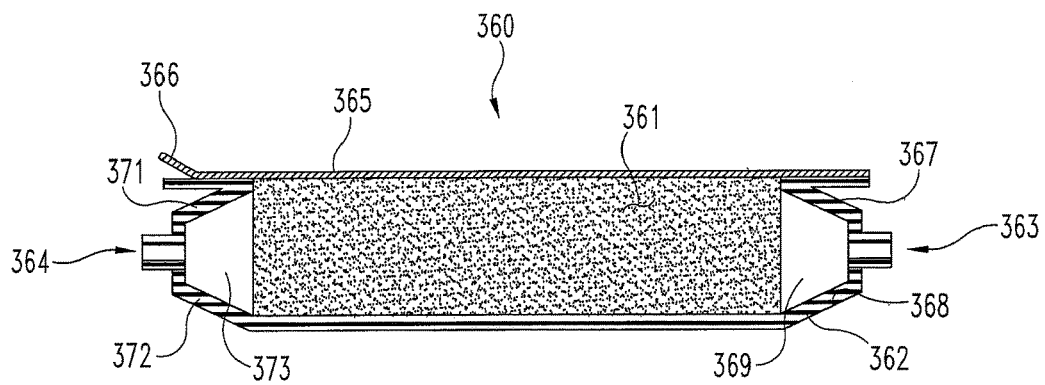

Referring now to FIG. 16, shown is another embodiment of a cell growth substrate article 360. Article 360 is similar in many respects to article 350 discussed above, and thus has features which are correspondingly numbered except in the "360" series. Article 360 further includes fluid distribution features associated with at least the fluid entry opening 363 and preferably with both that opening and fluid exit opening 364. Desirably, these features facilitate a substantially plug flow of liquid through article 360, with the plug having a cross sectional dimension substantially in the shape of the cross section of substrate 361. This will help to evenly distribute the cells through the substrate 361. For these purposes, tray or other encapsulating material 362 defines diverting walls 367 and 368 which diverge as they travel away from opening 363 and toward the periphery of cell growth substrate 361. Desirably, the inner surfaces of diverging walls 367 and 368 diverge two points substantially at the outer periphery of cell growth substrate 361. In this fashion, fluids entering opening 363 will fill the defined void 369 proximal of substrate 361, whereafter pressure of fluid entering opening 363 will be evenly distributed and cause a substantial plug flow through the substrate 361 across its cross sectional dimension. Fluids traversing substrate 361 will then be collected in void 373 defined by walls 371 and 372 which converge in the direction of exit opening 364. These and other features for facilitating a substantial plug flow across the substrate 361 within article 360 are contemplated in accordance with the invention.

Cell Growth Substrate Materials for Use in Inventive Embodiments

As noted above, cell growth substrates of and used in the invention can comprise extracellular matrix (ECM) tissue. The ECM tissue can be obtained from a warm-blooded vertebrate animal, such as an ovine, bovine or porcine animal. For example, suitable ECM tissue include those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. ECM tissues comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

ECM tissue when used in the invention is preferably decellularized and highly purified, for example, as described in U.S. Pat. No. 6,206,931 to Cook et al. or U.S. Patent Application Publication No. US2008286268 dated Nov. 20, 2008, publishing U.S. patent application Ser. No. 12/178,321 filed Jul. 23, 2008, all of which are hereby incorporated herein by reference in their entirety. Preferred ECM tissue material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 or U.S. Patent Application Publication No. US2008286268 may be characteristic of any ECM tissue used in the present invention.

In certain embodiments, the ECM tissue material used as or in the cell growth substrate will be a membranous tissue with a sheet structure as isolated from the tissue source. The ECM tissue can, as isolated, have a layer thickness that ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction.

The ECM tissue material may include one or more bioactive agents native to the source of the ECM tissue material and retained in the ECM tissue material through processing. For example, a submucosa or other remodelable ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain from the source tissue one or more bioactive components that induce, directly or indirectly, a cellular response such as a change in cell morphology, proliferation, growth, protein or gene expression.

Submucosa-containing or other ECM materials used in the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material used in the invention. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive graft compositions herein can incorporate xenograft ECM material (i.e., cross-species material, such as tissue material from a non-human donor to a human recipient), allograft ECM material (i.e., interspecies material, with tissue material from a donor of the same species as the recipient), and/or autograft ECM material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM tissue material will be xenogenic relative to the patient receiving the graft, and any added cells or other exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human cells and/or serum proteins and/or other material(s) as described herein, those exogenous materials being naturally derived and/or recombinantly produced.

When used in the invention, ECM materials can be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In additional embodiments, substrates of the invention can be made from ECM's or other collagenous materials that have been subjected to processes that expand the materials. In certain forms, such expanded materials can be formed by the controlled contact of an ECM material with a denaturing agent such as one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a substrate. Illustratively, the expanded material can be enriched with bioactive components, comminuted, dried, and/or molded, etc., in the formation of a substrate of a desired shape or configuration. In certain embodiments, a dried substrate formed with the expanded ECM material can be highly compressible and/or expandable.

Treatment of an ECM material with a denaturant, such as an alkaline material, can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein can be conducted so as to not significantly disrupt the intramolecular and intermolecular bonds, but denature the material to an extent that provides to the material an increased processed thickness, e.g. at least twice the naturally-occurring thickness. ECM materials that can be processed to make expanded materials for use as substrates can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

The expanded ECM material can then be processed to provide foam or sponge substrates, e.g. by comminuting, casting, and drying the processed material. Additional information concerning expanded ECM materials and their preparation is found in United States Patent Application Publication No. US20090326577 published Dec. 31, 2009, publishing U.S. patent application Ser. No. 12/489,199 filed Jun. 22, 2009, which is hereby incorporated herein by reference in its entirety.

In addition to or as an alternative to ECM materials, the cell growth substrate used in the invention may be comprised of other suitable materials. Illustrative materials include, for example, synthetically-produced substrates comprised or natural or synthetic polymers. Illustrative synthetic polymers can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; or resorbable synthetic polymer materials such as polylactic acid, polyglycolic acid or copolymers thereof, polyanhydride, polycaprolactone, polyhydroxy-butyrate valerate, polyhydroxyalkanoate, or another biodegradable polymer or mixture thereof. Preferred cell growth substrates comprised of these or other materials will be porous matrix materials configured to allow cellular invasion and ingrowth into the matrix.

Cells for Use in Inventive Embodiments

Any one or any combination of a wide variety of cell types can be used in cellular graft-related compositions and methods of the invention. For example, the cells can be skin cells, skeletal muscle cells, cardiac muscle cells, lung cells, mesentery cells, or adipose cells. The adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

In some embodiments, the cells incorporated in the cellular grafts are, or include, endothelial progenitor cells (EPCs). Preferred EPCs for use in the invention are endothelial colony forming cells (ECFCs), especially ECFCs with high proliferative potential. Suitable such cells are described for example in U.S. Patent Application Publication No. 20050266556 published Dec. 1, 2005, publishing U.S. patent application Ser. No. 11/055,182 filed Feb. 9, 2005, and U.S. Patent Application Publication No. 20080025956 published Jan. 1, 2008, publishing U.S. patent application Ser. No. 11/837,999, filed Aug. 13, 2007, each of which is hereby incorporated by reference in its entirety. Such ECFC cells can be a clonal population, and/or can be obtained from umbilical cord blood of humans or other animals. Additionally or alternatively, the endothelial colony forming cells have the following characteristics: (a) express the cell surface antigens CD31, CD105, CD146, and CD144; and/or (b) do not express CD45 and CD14; and/or (c) ingest acetylated LDL; and/or (d) replate into at least secondary colonies of at least 2000 cells when plated from a single cell; and/or (e) express high levels of telomerase, at least 34% of that expressed by HeLa cells; and/or (f) exhibit a nuclear to cytoplasmic ratio that is greater than 0.8; and/or (g) have cell diameters of less than about 22 microns. Any combination of some or all of these features (a)-(g) may characterize ECFCs used in the present invention.

In other embodiments, the cells incorporated in the cellular grafts are, or include, muscle derived cells, including muscle derived myoblasts and/or muscle derived stem cells. Suitable such stem cells and methods for obtaining them are described, for example, in U.S. Pat. No. 6,866,842 and U.S. Pat. No. 7,155,417, each of which is hereby incorporated herein by reference in its entirety. The muscle derived cells can express desmin, M-cadherin, MyoD, myogenin, CD34, and/or Bcl-2, and can lack expression of CD45 or c-Kit cell markers.

In still other embodiments, the cells incorporated in the cellular grafts are, or include, stem cells derived from adipose tissue. Suitable such cells and methods for obtaining them are described for example in U.S. Pat. No. 6,777,231 and U.S. Pat. No. 7,595,043, each of which is hereby incorporated herein by reference in its entirety. The cellular population can include adipose-derived stem and regenerative cells, sometimes also referred to as stromal vascular fraction cells, which can be a mixed population including stem cells, endothelial progenitor cells, leukocytes, endothelial cells, and vascular smooth muscle cells, which can be adult-derived. In certain forms, cellular grafts of the present invention can be prepared with and can include adipose-derived cells that can differentiate into two or more of a bone cell, a cartilage cell, a nerve cell, or a muscle cell.

Medical Treatments with Cellular Grafts

Cellular grafts of and prepared in accordance with the invention can be used in a wide variety of clinical applications to treat damaged, diseased or insufficient tissues, and can be used in humans or in non-human animals. Such tissues to be treated may, for example, be muscle tissue, nerve tissue, brain tissue, blood, myocardial tissue, cartilage tissue, organ tissue such as lung, kidney or liver tissue, bone tissue, arterial or venous vessel tissue, skin tissue, and others.

In certain embodiments, the cellular grafts can be used to enhance the formation of blood vessels in a patient, for example to alleviate ischemia in tissues. Direct administration of blood vessel-forming cellular grafts, for example grafts containing endothelial colony forming cells or other endothelial progenitor cells, to an ischemic site can enhance the formation of new vessels in the affected areas and improve blood flow or other outcomes. The ischemic tissue to be treated may for example be ischemic myocardial tissue, e.g. following an infarction, or ischemic tissue in the legs or other limbs such as occurs in critical limb ischemia. The cellular graft administered to the ischemic tissue can be a flowable graft material, and in particular an injectable graft material, as disclosed herein.

The cellular grafts can also be used to enhance the healing of partial or full thickness dermal wounds, such as skin ulcers, e.g. diabetic ulcers, and burns. Illustratively, the administration of grafts containing endothelial colony forming cells or other endothelial progenitor cells to such wounds can enhance the healing of the wounds.

In other applications, the cellular grafts can be used to generate muscle tissue at a target site, for example in the treatment of skeletal muscle tissue, smooth muscle tissue, myocardial tissue, or other tissue. Illustratively, cellular grafts of the invention containing muscle derived myoblasts can be delivered, e.g. by injection, into muscle tissue of a sphincter such as a urinary bladder sphincter to treat incontinence.

It will be understood that all cell-containing graft material embodiments as described herein, and method embodiments as described herein, can be prepared and conducted using cell-seeding devices and systems as described herein, for example including generally the steps of loading the substrate material into the cell-seeding device, loading a cellular composition into the cell-seeding device, and combining the substrate material and cells at least in part, and potentially completely, through the operation of the cell-seeding device. When other components described herein, such as a preconditioning medium, gel or gellable material, etc., are used, they can be charged to the appropriate chamber or passage of the cell-seeding device for operation and combination with the other material(s), as generally described, under the action of the cell-seeding device. Those skilled in the art will readily understand these combinations of features and embodiments described herein, which constitute further aspects of the invention. The cell-seeded graft material can then be obtained from the cell-seeding device, and optionally administered to a patient, including a human patient, e.g. for the medical indications identified herein.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

The invention claimed is:

1. A cell growth substrate, comprising: a cell growth substrate for supporting the growth of cells, the cell growth substrate including at least one elongate tubular passage, the elongate tubular passage having passage walls defining a lumen extending from a first lumen opening at a surface of the cell growth substrate into an interior region of the cell growth substrate, with said lumen configured to receive flow of a cell-containing liquid medium to distribute cells into the interior region of the cell growth substrate; wherein the cell growth substrate includes a cell growth substrate body comprised of a porous matrix material suitable for supporting cellular growth, with the cell growth substrate body including a first decellularized extracellular matrix tissue sheet and a second decellularized extracellular matrix tissue sheet, the first decellularized extracellular matrix sheet connected to the second decellularized extracellular matrix tissue sheet in such a fashion as to define the at least one elongate tubular passage between the first sheet and the second sheet, the passage walls of the elongate tubular passage having (i) a first passage wall portion defined by a face of the first decellularized extracellular matrix tissue sheet, (i) a second passage wall portion defined by a face of the second decellularized extracellular matrix tissue sheet, (W) a first seam defined by a first connection between the face of the first decellularized extracellular matrix tissue sheet and the face of the second decellularized extracellular matrix sheet, and (iv) a second seam defined by a second connection between the face of the first decellularized extracellular matrix tissue sheet and the face of the second decellularized extracellular matrix tissue sheet; and the first decellularized extracellular matrix tissue sheet and the second decellularized extracellular matrix tissue sheet being connected to one another along a connected region surrounding the at least one elongate tubular passage.

2. The cell growth substrate of claim 1, also comprising a synthetic polymeric tubular element exterior of the substrate and fluidly coupled to the lumen opening.

3. The cell growth substrate of claim 1, comprising a plurality of said tubular passages.

4. The cell growth substrate of claim 1, wherein the at least one elongate tubular passage includes at least one primary tubular passage with, at least one secondary tubular passage branching from the primary tubular passage.

5. The cell growth substrate of claim 1 wherein the tubular passage extends from the first lumen opening to a second lumen opening spaced on said substrate from the first lumen opening.

6. The cell growth substrate of claim 1, wherein the tubular passage terminates within the substrate.

7. The cell growth substrate of claim 1, wherein the first decellularized extracellular matrix tissue and second decellularized extracellular matrix tissue sheets are remodelable collagenous extracellular matrix sheet materials.

8. The cell growth substrate of claim 1, wherein the first decellularized extracellular matrix tissue sheet and the second decellularized extracellular matrix tissue sheet retain growth, factors, glycosaminoglycans, and proteoglycans from an animal source tissue.

9. The cell growth substrate of claim 1, wherein the at least one elongate tubular passage comprises a tortuous tubular passage.

10. The cell growth substrate of claim 9, wherein the tortuous tubular passage includes a first plurality of bends occurring opposite a second plurality of bends, with bends of the first plurality of bends and the second plurality of bends situated in opposed directions.

11. The cell growth substrate of claim 1, wherein the first decellularized extracellular matrix tissue sheet is bonded, fused, glued, or crosslinked to the second decellularized extracellular matrix tissue sheet in the connected region.

12. The cell growth substrate of claim 1, comprising a plurality of said tubular passages, and further wherein the tubular passages are separated from one another by intervening connected regions in which the face of the first decellularized extracellular matrix tissue sheet is connected to the face of the second decellularized extracellular matrix tissue sheet.

13. The cell growth substrate of claim 12, comprising tubular elements comprising a persistent or bioresorbable polymer, the tubular elements received within the tubular passages.

14. The cell growth substrate of claim 13, wherein the tubular elements include walls that are porous or that have holes or perforations.

15. The cell growth substrate of claim 1, wherein the at least one elongate tubular passage includes a common feed passage fluidly coupled to a plurality of passages.

16. The cell growth substrate of claim 1, further comprising a cellular composition in the interior region of the cell growth substrate.

17. A method for preparing a cell-seeded material, comprising:
   providing the cell growth substrate of claim 1;
   connecting a cell growth substrate to a source of a liquid suspension of cells, the connecting including fluidly associating the elongate passage with a transport lumen of the source; and
   transporting amounts of the liquid suspension of cells through the transport lumen and into the elongate passage so as to deliver cells to the interior region of the substrate.

18. The method of claim 17, wherein said connecting includes inserting the growth substrate into a cell-seeding chamber having an input tube fluidly connected to the source of liquid suspension of cells, and fluidly coupling the input tube to the first lumen opening of the substrate.

* * * * *

UNITED STATES PATENT AND TRADEMARK OFFICE
CERTIFICATE OF CORRECTION

PATENT NO. : 10,071,187 B2  
APPLICATION NO. : 14/835005  
DATED : September 11, 2018  
INVENTOR(S) : Michael C. Hiles et al.

Page 1 of 1

It is certified that error appears in the above-identified patent and that said Letters Patent is hereby corrected as shown below:

In the Claims

Column 40, Line 15, replace "(i)" with --(ii)--

Column 40, Line 17, replace "(W)" with --(iii)--

Signed and Sealed this  
Sixteenth Day of July, 2019

Andrei Iancu  
*Director of the United States Patent and Trademark Office*